United States Patent [19]
Thompson et al.

[11] Patent Number: 5,800,465
[45] Date of Patent: Sep. 1, 1998

[54] SYSTEM AND METHOD FOR MULTISITE STEERING OF CARDIAC STIMULI

[75] Inventors: David L. Thompson; Gary W. King, both of Fridley; Gregory A. Hrdlicka, Plymouth, all of Minn.

[73] Assignee: Medtronic, Inc., Minneapolis, Minn.

[21] Appl. No.: 755,797

[22] Filed: Oct. 30, 1996

Related U.S. Application Data

[60] Provisional application No. 60/020,421, Jun. 18, 1996.
[51] Int. Cl.$^6$ .................. A61N 1/36; A61N 1/05
[52] U.S. Cl. .................. 607/9; 607/123; 607/122
[58] Field of Search ................ 607/4, 9, 11, 15, 607/122, 123, 129

[56] References Cited

U.S. PATENT DOCUMENTS

| | | | |
|---|---|---|---|
| 3,825,015 | 7/1974 | Berkovits | 128/404 |
| 3,942,536 | 3/1976 | Mirowski et al. | 128/419 D |
| 4,444,195 | 4/1984 | Gold | 607/122 |
| 4,708,145 | 11/1987 | Tracker et al. | 128/419 D |
| 4,830,006 | 5/1989 | Haluska et al. | 128/419 PG |
| 4,880,005 | 11/1989 | Pless et al. | 128/419 PG |
| 5,007,436 | 4/1991 | Smits | 128/786 |
| 5,014,696 | 5/1991 | Mehra | 128/419 D |
| 5,095,916 | 3/1992 | Smits | 128/784 |
| 5,099,838 | 3/1992 | Bardy | 128/419 D |
| 5,163,427 | 11/1992 | Keimel | 128/419 D |
| 5,174,288 | 12/1992 | Bardy et al. | 128/419 D |
| 5,181,511 | 1/1993 | Nickolls et al. | 128/419 PG |

(List continued on next page.)

FOREIGN PATENT DOCUMENTS

WO 95/19804   7/1995   WIPO.

OTHER PUBLICATIONS

Saksena, Sanjeev, M.D., et al., "Initial Clinical Experience with Endocardial Defibrillation Using an Implantable Cardioverter/Defibrillator With a Triple–Electrode System," Arch Intern Ned—vol. 149, Oct. 1989.

Scott, Steven et al., Ventricular and Atrial Defibrillation Using New Transvenous Tripolar and Bipolar Leads with 5 French Electrodes and 8 French Subcutaneous Catheters, PACE, vol. 14, Nov., 1991.

Holsheimer, Jan et al., Effects of Various Contact Combination of Paresthesia Coveragein Spinal Cord Stimulation,: Institute for Biomedical Technology, University of Twente, Enschede, The Netherlands.

Markowitz, Toby, et al.,"Atrial and Ventricular Capture Detection and Threshold–Seeking Pacemaker," (P–3338), Application for U.S. Letters Patent, filed Aug. 16, 1995.

*Primary Examiner*—William E. Kamm
*Assistant Examiner*—Carl H. Layno
*Attorney, Agent, or Firm*—Thomas F. Woods; Harold R. Patton

[57] ABSTRACT

A system and corresponding method for steering stimulus pulses to one or more selected cardiac sites are disclosed. An apparatus and corresponding method permit improved capture and easy adjustment of the stimulus pulse when the threshold level changes, without simply increasing stimulus power or replacing the implanted lead. Substantially concurrent pulses may be delivered across one, two or more anode electrodes and a corresponding common or cathode electrode, where the pulse amplitude, pulse duration or pulse phase characteristics of each individual component pulse are adjusted to permit the resulting composite pulse to be steered or directed towards a desired target cardiac site. Different embodiments of the apparatus and corresponding method include those which permit the steering of pacing pulses in the left atrium or in multiple chambers, use of an improved single lead system having electrodes floating in the atrium, steering of atrial pulses to provide an enhancement of a VDD system, steering of atrial or ventricular defibrillation stimuli, and steering stimuli for arrhythmia prevention. In yet other embodiments, the steered pulse system is combined with capture detection and automatic adjustment of the steering parameters.

42 Claims, 21 Drawing Sheets

U.S. PATENT DOCUMENTS

| | | | |
|---|---|---|---|
| 5,191,901 | 3/1993 | Dahl et al. | 607/129 |
| 5,199,428 | 4/1993 | Obel et al. | 128/419 C |
| 5,224,476 | 7/1993 | Ideker et al. | 607/9 |
| 5,265,601 | 11/1993 | Mehra | 607/9 |
| 5,269,298 | 12/1993 | Adams et al. | 28/419 D |
| 5,271,395 | 12/1993 | Wahlstrand et al. | 607/9 |
| 5,281,219 | 1/1994 | Kallok | 607/42 |
| 5,306,291 | 4/1994 | Kroll et al. | 607/5 |
| 5,324,309 | 6/1994 | Kallok | 607/5 |
| 5,331,966 | 7/1994 | Bennett et al. | 128/696 |
| 5,336,253 | 8/1994 | Gordon et al. | 607/122 |
| 5,344,429 | 9/1994 | Smits | 607/5 |
| 5,344,430 | 9/1994 | Berg et al. | 607/8 |
| 5,370,665 | 12/1994 | Hudrlik | 607/9 |
| 5,387,233 | 2/1995 | Alferness et al. | 607/125 |
| 5,403,351 | 4/1995 | Saksena | 607/4 |
| 5,403,356 | 4/1995 | Hill et al. | 607/14 |
| 5,423,873 | 6/1995 | Neubauer et al. | 607/68 |
| 5,441,525 | 8/1995 | Shelton et al. | 607/23 |
| 5,447,519 | 9/1995 | Peterson | 607/5 |
| 5,456,706 | 10/1995 | Pless et al. | 607/122 |
| 5,501,703 | 3/1996 | Holsheimer et al. | 407/46 |
| 5,514,161 | 5/1996 | Limousin | 607/9 |
| 5,531,764 | 7/1996 | Adams et al. | 607/5 |
| 5,545,204 | 8/1996 | Cammilli et al. | 607/123 |

SYSTEM AND METHOD FOR MULTISITE STEERING OF CARDIAC STIMULI

This application claims the benefit of the filing date of a U.S. provisional application entitled "A Method and Apparatus to Steer Multisite Pacing or Defibrillation Stimulus" to Thompson et al. filed Jun. 18, 1996, having Provisional U.S. patent application Ser. No. 60/020,421 and Attorney Docket No. P-4641.

FIELD OF THE INVENTION

The present invention relates to the field of systems and methods of cardiac stimulation, and more particularly to cardiac pacing and defibrillating systems having the capability to steer pacing or defibrillation pulses or stimuli from one or a plurality of leads to selected cardiac stimulation sites.

BACKGROUND

Efficient and reliable delivery of pacing and defibrillation pulses to a desired cardiac site is known to be of great importance. A great amount of effort has been expended in recent years to improve the efficiency and reliability of such systems. For example, significant improvements have been made in high efficiency batteries, low power consumption chip circuitry and programmability for optimizing pacing thresholds. Nevertheless, those improvements have not provided a completely adequate solution to the persisting problem of the relatively short battery life that characterizes most pacemakers and defibrillators owing to the heavy battery drain rates characteristic of such devices.

If energy from a lead is delivered inefficiently to a cardiac site, a greater effective threshold for capture results which, in turn, increases power drain and decreases pacemaker longevity. Where failure to capture occurs a desired pacing function is simply not performed. Backup circuitry and software may detect loss of capture and respond by delivering pacing pulses of greater energy. This approach, however, leads to other problems such as patient discomfort and annoyance resulting from the higher voltage levels, and the need to reprogram the pacemaker.

In implantations of conventional pacemakers, and especially in implantations of single chamber pacemakers, a suitable chronic threshold may be obtained by carefully anchoring the distal tip of the lead to the patient's heart wall by using a tined lead or other fixation means, and then reprogramming the pacemaker soon thereafter to obtain a satisfactory chronic threshold. In the case where only one site is being stimulated and the electrode is anchored close to an optimum pacing site, the problem is minimal.

In a dual chamber pacemaker system a second lead may be introduced into the atrium and anchored. However, this complicates and lengthens the implant procedure and results in two thresholds having to be programmed. One answer to this problem is provided by the VDD pacemaker system with a single lead, the lead having a conventional unipolar or bipolar electrode arrangement disposed at its distal end, and a pair of "floating" electrodes positioned in the atrium. The floating atrial electrodes are not actively affixed to the atrial wall and consequently cannot provide the performance equivalent to active fixation electrodes. As a result, floating electrodes typically sense atrial signals reasonably well but cannot deliver effective pacing pulses.

Although some attempts have been made to design floating electrodes that will effect atrial pacing, those attempts have not met with great success due to the physical distance between the electrodes and the intended atrial pacing site. In short, whenever electrodes are not well anchored at the pacing site the problems of achieving and maintaining an efficient pacing threshold are magnified.

The advent of certain newer types of pacing systems has further magnified the problem of achieving efficient pacing where the pacing electrode cannot be affixed directly to the desired pacing site. One such system is a biatrial pacing system, where sensing and stimulation of the right and left atria improves the cardiac output of patients with inappropriate intra-atrial delays.

Some aspects relating to the bi-atrial pacing system are described in U.S. Pat. No. 5,414,161, herein incorporated by reference in its entirety. The '161 patent discloses right atrial sensing and pacing using conventional endocardial active fixation leads implanted in accordance with conventional right-sided DDD pacing practice. Left atrial sensing and pacing is typically accomplished by introducing either a pacing lead or a lead such as the Medtronic Model No. 2188 lead near the left atrium via the coronary sinus. The Model No. 2188 lead is described in U.S. patent application Ser. No. 08/639,458, filed Apr. 29, 1996, incorporated herein by reference in its entirety.

It is known that coronary sinus leads are difficult to place. Furthermore, it is often difficult to find an initial location in the coronary sinus where an adequate threshold may be obtained. Those difficulties during implantation result in lengthened procedures, patient discomfort, increased costs and higher thresholds. It is also known that coronary sinus electrodes often move or shift after implantation, resulting in chronic threshold "shift". This often causes loss of capture and requires the patient's pacemaker to be reprogrammed to higher pulse amplitudes or widths. This, in turn, can result in a reduction in the longevity of the pacemaker. Reprogramming the device often results in an inability to capture, or the provision of an inadequate safety margin. If so, the physician must reposition the lead during an additional surgical procedure, thereby increasing costs and risks of infection.

Another potentially advantageous but infrequently used pacing system is the single lead DDD pacing system, where pacing and sensing are accomplished in both atrial and ventricular chambers with a single lead having one or more electrodes. U.S. Pat. No. 5,265,601 describes such a system for pacing the atrium and the ventricle from a single electrode positioned in the coronary sinus or deep cardiac vein. In such a system, stimulus amplitude is varied so that the atrial pacing pulse has a relatively low amplitude and the ventricular pacing pulse has a relatively high amplitude. The respective pulses are timed in accordance with the pacemaker's tracking of the cardiac cycle.

While the foregoing system provides acceptable results under some conditions, premature atrial contractions (PACs), premature ventricular contractions (PVCs), 2:1 block, oversensing of far-field R waves and the like can cause such systems to become confused, resulting in disrupted timing and loss of function. Additionally, the signal output in such a system is omnidirectional in respect of the electrode configuration. This results in threshold variation and low capture efficiency. Furthermore, due to the omnidirectional nature of the signal, either the V or A pacing pulse may cause unintended stimulation of the opposing chamber if it is stimulated outside the refractory period. Finally, such a system limits the maximum AV delay to a value less than the refractory period of the atrial myocardial tissue, because otherwise the V pace pulse would stimulate the atrium.

The ability to deliver stimulus pulses to desired locations with improved site resolution is desired in defibrillation systems and in treating cardiac arrhythmias such as atrial tachycardia. What is needed is a system that provides the maximum flexibility and control without employing multiple leads having anchored electrodes at each specific site of interest.

A method of stimulating the spinal cord is disclosed in U.S. Pat. No. 5,501,703, incorporated herein by reference in its entirety. The '703 patent discloses a multichannel apparatus for epidural spinal cord stimulation based on the observation that a stimulation induced paresthesia pattern may be focussed and changed by using multiple electrodes and changing the parameters of the delivered stimulus pulses. The superposition of potential electric fields generated by simultaneous stimulation provided by multiple pulse generators and corresponding electrodes results in a significant change in the size and shape of the stimulated spinal cord area.

The '703 patent describes a lead as being implanted a few millimeters from the spinal cord with an electrode array disposed in the epidural space. Changes in the parameters corresponding to the individual stimulus pulses provides control over which nerve fibers adjacent to the electrode array are excited, and which are not. While this technique has been found successful in the limited area of spinal cord stimulation, no similar application has been developed for pacing or cardiac stimulation.

Pacing and defibrillating devices, systems and methods are well known in the art, some examples of which may be found in the issued U.S. Patents listed in Table 1 below.

TABLE 1

Prior Art Patents

| Patent No. | Title |
| --- | --- |
| 3,825,015 | Single Catheter for Atrial and Ventricular Stimulation |
| 3,924,536 | Cardioverting Device Having Single Intravascular Catheter Electrode System and Method for Its Use |
| 4,708,145 | Sequential-Pulse, Multiple Pathway Defibrillation Method |
| 4,830,006 | Implantable Cardiac Stimulator for Detection and Treatment of Ventricular Arrhythmias |
| 4,880,005 | Pacemaker for Detecting and Terminating a Tachycardia |
| 5,007,436 | Cardioversion and Defibrillation Lead System |
| 5,014,696 | Endocardial Defibrillation Electrode System |
| 5,095,916 | Cardioversion and Defibrillation Lead System |
| 5,009,838 | Endocardial Defibrillation Electrode System |
| 5,163,427 | Apparatus for Delivering Single and Multiple Cardioversion and Defibrillation Pulses |
| 5,174,288 | Method and Apparatus for Cardiac Defibrillation |
| 5,181,511 | Apparatus and Method for Antitachycardia Pacing Using a Virtual Electrode |
| 5,199,428 | Implantable Electrical Nerve Stimulation/Pacemaker with Ischemia for Decreasing Cardiac Workload |
| 5,265,601 | Dual Chamber Cardiac Pacing From a Single Electrode |
| 5,269,298 | Atrial Defibrillator and Method for Providing Synchronized Delayed Cardioversion |
| 5,271,395 | Method and Apparatus for Rate-Responsive Cardiac Pacing |
| 5,281,219 | Multiple Stimulation Electrodes |
| 5,306,291 | Optimal Energy Steering for an Implantable Defibrillator |
| 5,324,309 | Overlapping Pulse Cardioversion or Defibrillation |
| 5,331,764 | Implantable Defibrillator System and Method Having Successive Changeable Defibrillation Waveforms |
| 5,331,966 | Subcutaneous Multi-Electrode Sensing System, Method and Pacer |
| 5,336,253 | Pacing and Cardioversion Lead Systems with Shared Lead Conductors |
| 5,344,429 | Pulse Routing Apparatus for Cardioversion and Defibrillation |
| 5,344,430 | Method and Apparatus for Termination of Ventricular Tachycardia and Ventricular Fibrillation |
| 5,370,665 | Medical Stimulation With Multiple Operational Amplifier Output Stimulation Circuits |
| 5,387,233 | Intravenous Cardiac lead with Improved Fixation and Method |
| 5,403,351 | Method and Transvenous Defibrillation/Cardioversion Employing an Endocardial Lead System |
| 5,403,356 | Method and Apparatus for Prevention of Atrial Tachy Arrhythmia |
| 5,423,873 | Device for Stimulating Living Tissue |
| 5,441,525 | Pacemaker with Vasovagal Syncope Detection |
| 5,447,519 | Method and Apparatus for Discrimination of Monomorphic and Polymorphic Arrhythmias and for Treatment Thereof |
| 5,456,706 | Cardiac Defibrillation Lead Having Defibrillation and Atrial Sensing Electrodes |
| 5,501,703 | Multichannel Apparatus for Epidural Spinal Cord Stimulator |
| 5,514,161 | Methods and Apparatus for Controlling Atrial Stimulation in a Double Atrial Triple Chamber Cardiac Pacemaker |
| WO 95/1980 PCT | Multichannel Apparatus for Epidural Spinal Cord Stimulation |

All patents listed in Table 1 hereinabove are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has certain objects. That is, the present invention provides solutions to problems existing in the prior art. The objects of the present invention include, but are not limited to, providing a pacing or defibrillating system that is capable of:

(a) reducing the threshold required to stimulate the heart;

(b) using power at a reduced rate respecting prior art systems;

(c) continuing to steer pulses of electrical energy to specific optimum intra-cardiac sites even though a lead shifts position in or near the heart;

(d) employing fewer leads to pace or defibrillate the heart;

(e) having a reduced physical size, but nevertheless offering the same or better performance, respecting prior art pacemakers or defibrillators;

(f) pacing the atrium and ventricle using a single lead;

(g) reducing the amount of medical hardware that must be implanted in a patient to obtain reliable pacing or defibrillation of the heart, and (h) reducing the amount of pain felt by a patient during atrial defibrillation owing to more accurate steering of defibrillation pulses.

What is desired for cardiac applications is a system and corresponding method to effectively "steer" cardiac stimulus pulses so that they efficiently capture or defibrillate a selected heart chamber, or otherwise control a cardiac arrhythmia. Such a system and method must take into account the fact that in cardiac applications the chambers are separate and are not similar to nerves aligned along a single spinal cord. Rather, cardiac muscle tissue in one or more separate chambers must be stimulated without having an array of electrodes positioned substantially adjacent to the various stimulus target locations.

The present invention provides system and method embodiments for pacing or otherwise stimulating one or more cardiac sites from a proximately positioned set of electrodes, where the individual pulse parameters of a plurality of pulse components are controlled in such a manner that the outputs are combined into composite stimulus pulses. The present invention permits efficient steering of each such composite pulse to a selected site and adjustment of steering parameters to adapt to threshold changes. By varying the field of stimulation over a range of cardiac areas, the present invention allows a quicker implant procedure because the lead may be positioned in a general area such as the left atrium or the coronary sinus. Later an optimum threshold for stimulating in one or more areas may be selected and programmed through setting the various pulse parameters corresponding to each pacing or defibrillation pulse component of each composite stimulus pulse.

In a general system configuration the present invention provides at least one lead having three or more electrodes disposed thereon. During implantation the electrodes are positioned in a selected area within or proximate to the heart, and the resulting composite stimulus pulse is targeted or steered to one or more selected cardiac sites. In a simple embodiment of the present invention, three electrodes are employed: two active electrodes and one common electrode (or "ground") deliver two pulses, the two pulses being individual components of a composite pulse programmed to generate an electric stimulus steered toward a selected site. The various pulse component parameters are programmed. Those parameters include pulse magnitude (either amplitude or duration), polarity, and phase (timing). Each pulse is delivered between one of the active electrodes and the common electrode.

In a more complex arrangement, the lead has a number of electrodes (n) greater than three, and the electrodes are controllably connected through a switch matrix to be either active or common. This embodiment of the present invention provides steering control through both pulse parameter control and electrode selection. The control may also incorporate switching delivery of stimulus pulses and sensing to either a bipolar or unipolar arrangement for further optimization of pulse capture and accurate sensing In a further embodiment of the present invention, electrodes are spatially separated from one another along a lead. Those electrodes sense cardiac signals, which are compared to determine and verify the origin of the sensed signals as arising at specific sites in the atrium or the ventricle.

In a first specific embodiment of the present invention, a system and method of left atrial pacing are provided, where a lead having an array of two active electrodes and one common electrode is positioned in proximity to the left atrium in the coronary sinus. Composite pacing pulses are generated by producing two pulses from two separate generators, where each pulse is controlled at least in respect of amplitude and is delivered between an active electrode and a common electrode. Pulse parameters are preferably controlled to steer the area of tissue stimulation so that it sweeps from right, to center and to the left. Once output pulse parameters are optimized by standard threshold determination techniques, the values are stored in memory locations in the pacemaker. Optimizing output pulse stimulus parameters such as independently programmed pulse amplitude, pulse width, and degree of overlap (or phase) between pulses permits recapture and threshold optimization in the event of lead dislodgement. Thus, an additional surgical procedure for repositioning a migrated or dislodged lead becomes unnecessary.

A second embodiment of the present invention provides for DDD pacing from a single lead, the lead having at least two active electrodes and at least one common electrode positioned in the coronary sinus or deep cardiac vein. A different two pulse component composite stimulus is generated for each of the ventricular and atrial pulses, respectively. For the ventricular stimulus, a larger composite amplitude is employed and pulse is steered toward the ventricle by appropriate adjustment of the parameters of the pulse components delivered across each active electrode with respect to the common electrode. For the atrial stimulus, a smaller composite amplitude is employed and pulse parameters are varied to steer the resulting field toward the atrium. Pulses may be timed in accordance with the cardiac cycle, taking into account sensed signals from each chamber. The lead preferably has one or more additional sensing electrodes to enable discrimination of the direction from which heart signals emanate such that any ambiguities in respect of unusual signals such as PACs and PVCs may be resolved. In this embodiment of the present invention and others, the automatic threshold determination feature is preferably protected so that threshold variations may be used to automatically adjust pulse steering parameters for optimum performance.

In yet another embodiment of the present invention a single pass lead is used for DDD made pacing, where the lead has one or two electrodes for pacing and sensing in the ventricle, and an array of floating electrodes positioned in the atrium for pacing and sensing in the atrium. The atrial array preferably has three electrodes: two active electrodes and one common or indifferent electrode. Different pulses are delivered across each active/common pair, either simultaneously or with very little phase difference. Pulse parameters are adjusted as required to permit optimal steering of pacing pulses for enhanced stimulation.

In addition to the above embodiments of the present invention the system and method of the present invention may be utilized in other embodiments directed to atrial defibrillation, atrial arrhythmia prevention, ventricular defibrillation, and site specific anti-tachycardia therapy. The system and method of the present invention may also employ specific lead and pulse output subsystems.

One important feature and advantage of the present invention is that it permits stimulation pulses to be steered and delivered to selected intracardiac sites with an accuracy and spatial resolution heretofore not attainable in prior art pacing, cardioverting or defibrillating systems.

Other objects, features, advantages and embodiments of the present invention will become apparent upon reading the detailed description and the claims.

DETAILED DESCRIPTION OF THE PREFERRED EMBODIMENTS

In the claims and specification hereof, the term "active electrode" means an anode electrode towards and into which electrons flow, and the term "common electrode" means a cathode electrode from or away from which electrons flow.

Figure 1A:
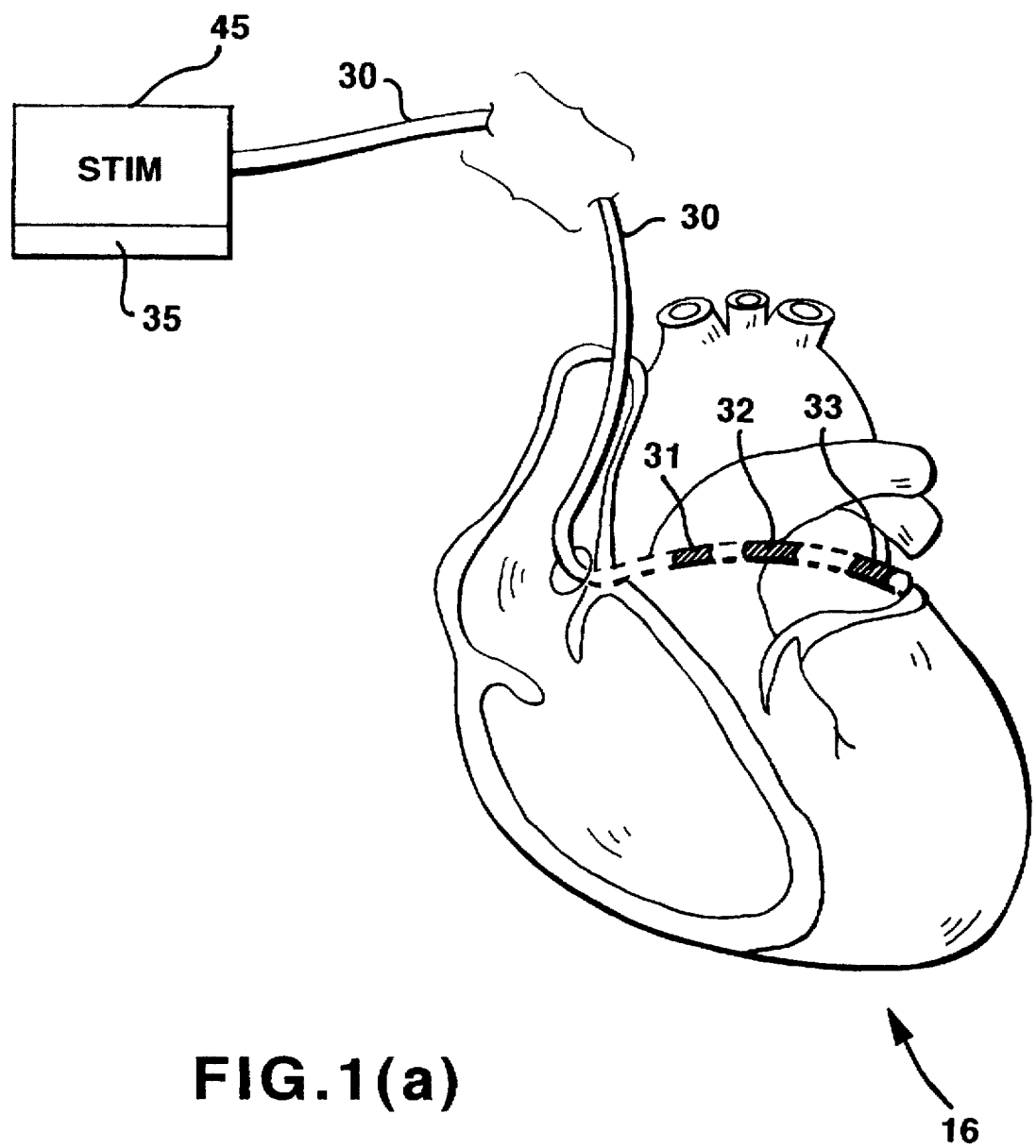
FIG. 1(a) illustrates a patient's heart and one embodiment of the present invention for steering stimulus pulses to different cardiac sites.

FIG. 1(a) shows a schematic diagram of a patient's heart and one embodiment of the present invention, where one lead of the present invention is disposed therewithin, and where the lead is configured and adapted to deliver and steer composite stimulus pulses to specific sites. The lead is positioned in at least a portion of the coronary sinus vein. FIG. 1(a) is illustrative, and is not intended to suggest all embodiments of the present invention.

Lead 30 is positioned with its distal end portion in the patient's coronary sinus, and has three electrodes 31,32,33, where electrode 32 is preferably a common electrode. In addition, stimulator case 35 may be used as a common electrode. Lead 30 is connected to stimulator 45 which is a pacemaker, a defibrillator, or a combined pacemaker-cardioverter-defibrillator stimulator. Lead 30 has conductors connecting pulse generator outputs from stimulator 34 to corresponding electrode pairs 31,32 and 33,32 for delivering composite pulses. Individual pulse parameters are chosen to steer the composite pulse to a specific site. For example, pulses may be steered to the right or left atrium from the location shown in FIG. 1(a), or to both the left atrium and left ventricle, or some other combination thereof.

Figure 1B:
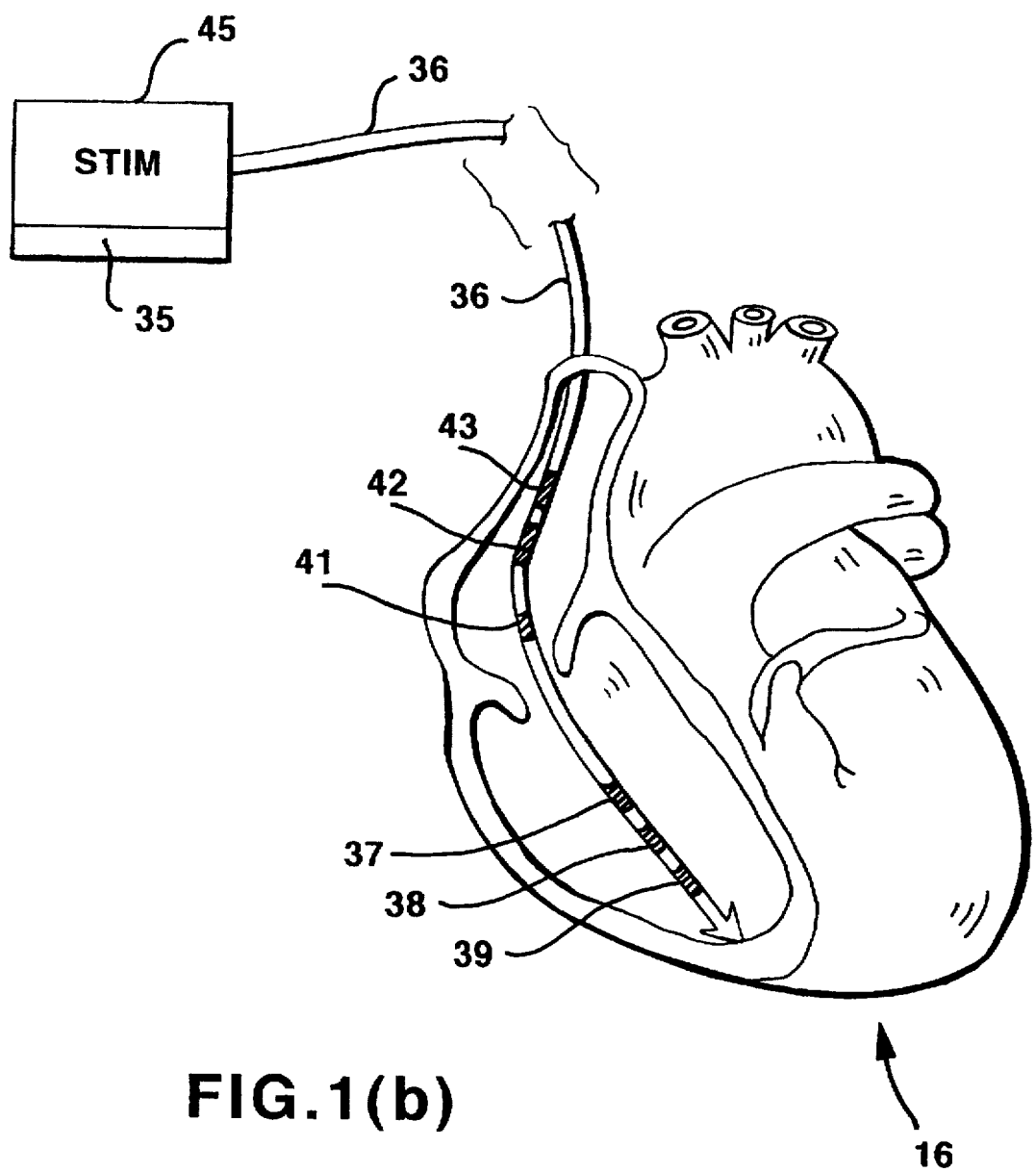
FIG. 1(b) illustrates a patient's heart and another embodiment of the present invention for steering stimulus pulses to different cardiac sites.

FIG. 1(b) shows a schematic diagram of a patient's heart and another embodiment of the invention, where one lead of the present invention is disposed therewithin, and where the lead is configured and adapted to deliver and steer composite stimulus pulses to specific sites. The lead is positioned in the right atrium and right ventricle. FIG. 1(b) is illustrative, and is not intended to suggest all embodiments of the present invention.

Lead 36 is shown in FIG. 1(b). Lead 36 is usually employed by itself, but may optionally be used in conjunction with lead 30 of FIG. 1(a). Lead 36 is likewise connected to stimulator 45 and may have either or both electrode sets 37, 38, 39 and 41, 42, 43 disposed thereon. Ventricular electrodes 37, 38, 39 are preferably connected to receive pulse component pulses across pairs 37, 38 and 39, 38 or may be connected between any one of such electrodes and case 35. Atrial electrodes 41, 42, 43 are preferably connected to receive pulse component pulses across pairs 41, 42 and 43, 42 or between any one of such electrodes and case 35.

Figure 1C:
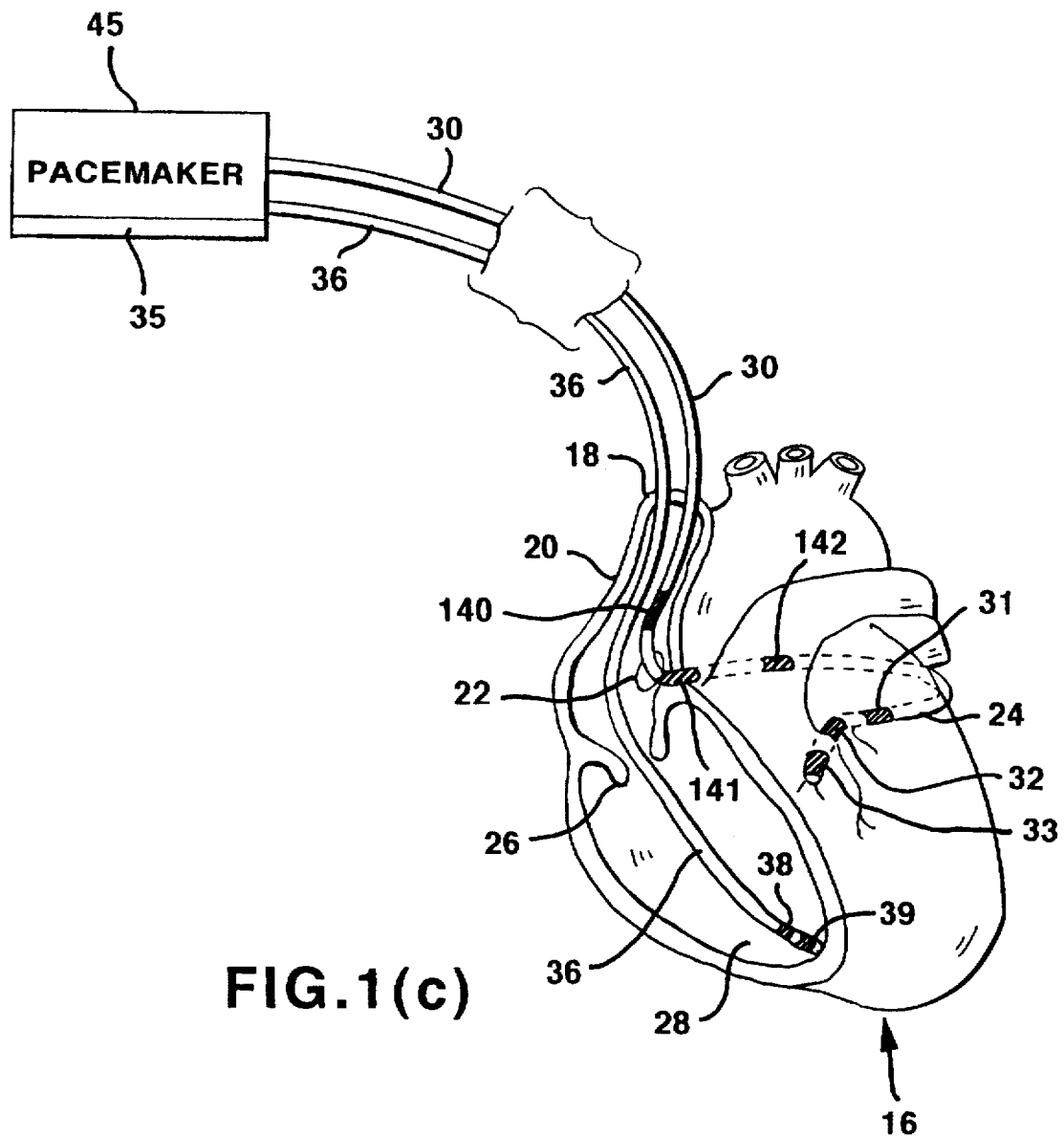
FIG. 1(c) illustrates a patient's heart and yet another embodiment of the present invention for steering stimulus pulses to different cardiac sites that is configured for one-, two-, three- or four chamber pacing.

FIG. 1(c) shows a schematic diagram of a patient's heart and yet another embodiment of the invention, where two leads of the present invention are disposed therewithin, and where the leads are configured and adapted to deliver and steer composite pacing pulses to a selected chamber, or to a selected plurality of chambers. Lead 30 is positioned in the coronary sinus vein, and connected to stimulator 45. Lead 36 is positioned in the right atrium and right ventricle. FIG. 1(c)

is illustrative, and is not intended to suggest all embodiments of the present invention.

Lead 30 is connected to stimulator 45. Lead 30 is preferably positioned in the coronary sinus vein such that center or common electrode 141 is located near the junction between the right and left atria. In this manner, active electrodes 140 and 142 may be used to stimulate either or both atria, according to the amplitudes and phases selected for each the individual pulses emitted by each pair of common and active electrodes 140, 141 and 142. In addition, lead 30 is preferably positioned in the coronary sinus vein such that electrode 32 is located near the junction between the left atrium and the left ventricle. In this manner, active electrodes 31 and 33 may be used to stimulate either the left atrium or the left ventricle, or both, according to the amplitudes and phases selected for each the individual pulses emitted by each pair of common and active electrodes 31, 32 and 33. Lead 36 is likewise connected to stimulator 45 and has electrode set 38, 39 disposed thereon for pacing stimulation of the right ventricle. Additionally, case 35 may be employed as a common or cathode electrode for any of electrodes 140, 142, 31, 33, or 39.

Figure 1D:
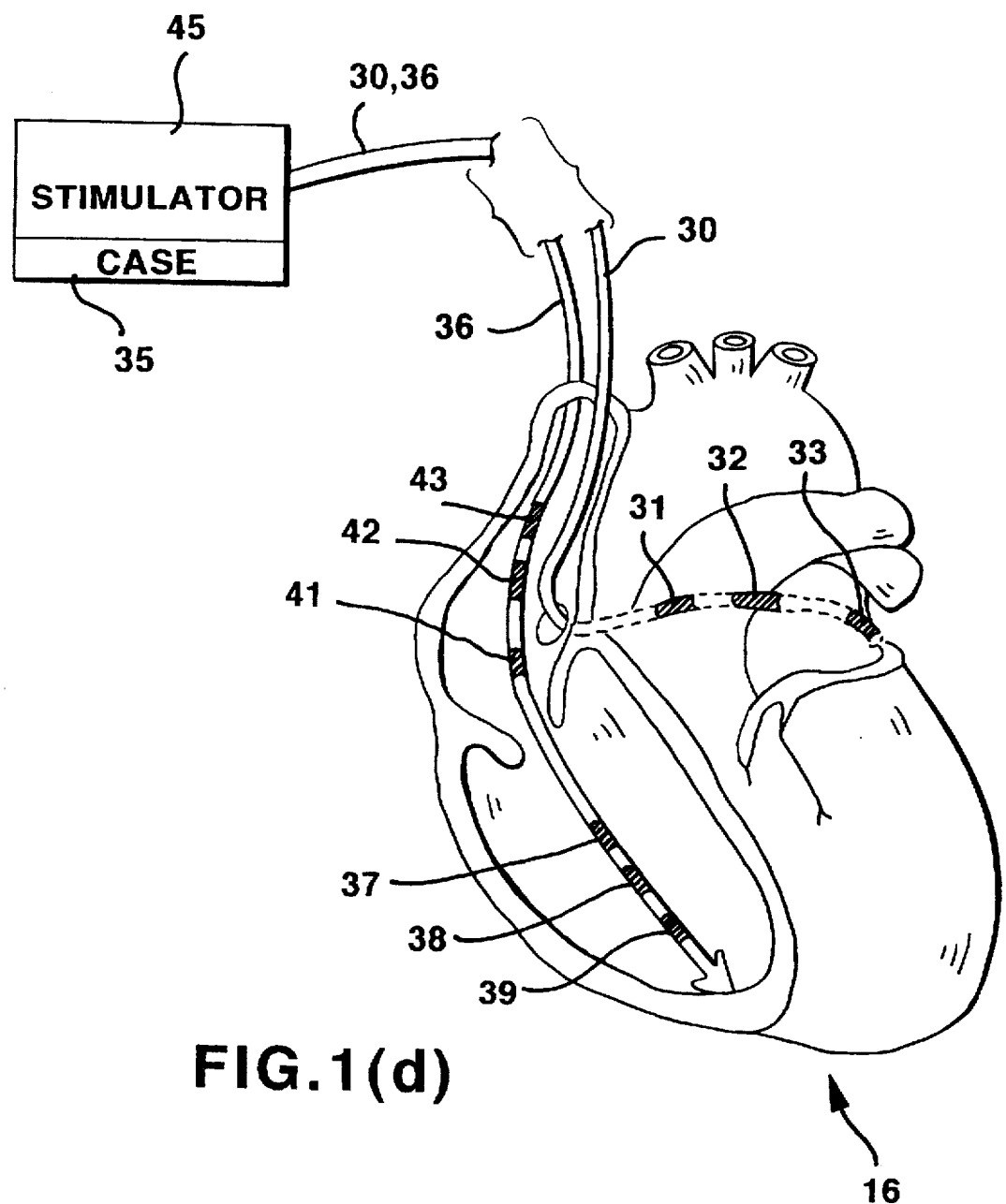
FIG. 1(d) illustrates a patient's heart and another embodiment of the present invention for steering stimulus pulses to different cardiac sites that is configured for one-, two-, three- or four chamber pacing.

FIG. 1(d) shows a schematic diagram of a patient's heart and still another embodiment of the invention, where two leads of the present invention are disposed therewithin, and where the leads are configured and adapted to deliver and steer composite pacing pulses to a selected chamber, or to a selected plurality of chambers. Lead 30 is positioned in the coronary sinus vein, and connected to stimulator 45. Lead 36 is positioned in the right atrium and right ventricle. FIG. 1(d) is illustrative, and is not intended to suggest all embodiments of the present invention.

In any selected electrode configuration of the present invention, appropriate control of individual pulse component parameters is utilized cause the resulting composite pulse to be steered to the desired location or cardiac site. For example, floating atrium electrodes 41,42,43 may be used for atrial pacing in a DDD mode with single pass lead 36. In any particular electrode configuration, selected or additional electrodes may sense cardiac signals. Although electrode sets comprising two active electrodes and one common electrode (e.g., two anodes and one cathode) are illustrated herein, the electrode sets may comprise a greater number of electrodes (n) and may be switchable in conjunction with the pacemaker or stimulator case as a common electrode.

For example, electrode sets may comprise three active electrodes separated by two common electrodes, three active electrodes positioned between four common electrodes where all active electrodes are disposed between two outlying common electrodes, four active electrodes separated by three common electrodes, four active electrodes positioned between five common electrodes where all active electrodes are disposed between two outlying common electrodes, and so on. FIGS. 10(a) through 10(f) show some of the foregoing embodiments of the leads of the present invention.

For intra-cardiac pacing applications, electrode surface areas preferably approximately 34–50 mm$^2$. Separation between each active electrode and a common electrode preferably exceeds about 7 mm. For electrode placement outside a cardiac chamber (such as in the coronary sinus), the separation between each neutral electrode and a common electrode preferably exceeds about 1 cm. The corresponding distance between two active electrodes preferably exceeds about 1.4 cm, and most preferably exceeds about 2 cm. In defibrillation and other cardioversion applications, electrode surface areas and inter-electrode spacings are greater.

Figure 2:
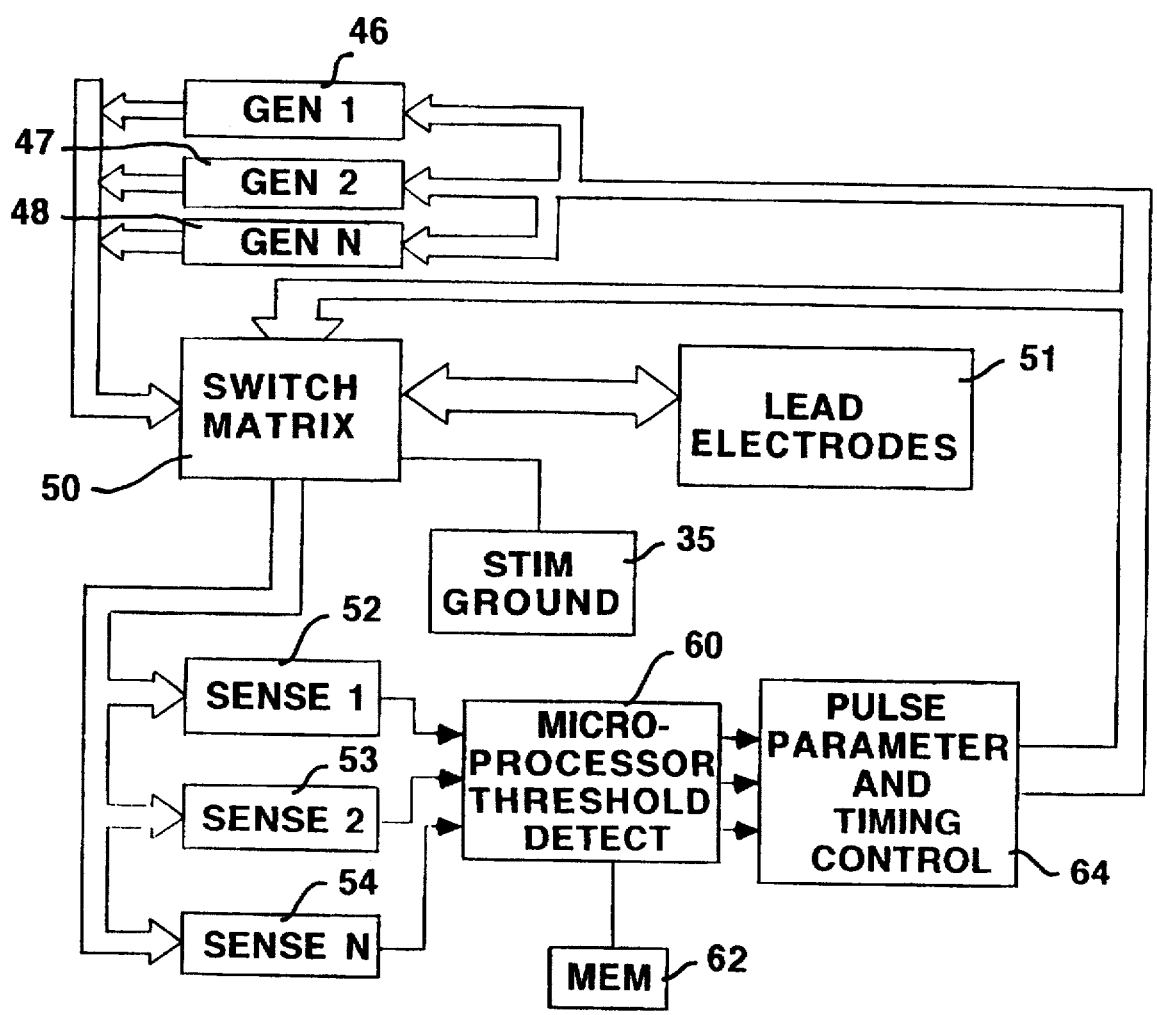
FIG. 2 shows a block diagram of the primary system components of the present invention for steering pulses from electrodes positioned within or proximate to the patient's heart to one or more cardiac sites.

FIG. 2 shows a block diagram of the primary components of stimulator 45 of the present invention. Generators 1,2 . . . . . . n are shown at 46,47,48 and are generators for producing pulse components. The generators are enabled or not, and are controlled in respect of pulse parameters and timing by pulse parameter and timing control block 64. The selected generator outputs are connected through switch matrix 50 (also controlled by block 64) so that selected pulse components are connected to selected electrodes as shown at 51; one or more generator outputs may be connected between a selected electrode and stimulator ground 35. Sensed signals are routed through switch matrix 50 to sense circuits 52,53, 54, the outputs of which are connected to microprocessor/threshold detect block 60.

Block 60 performs all the usual and necessary logic and timing functions of a stimulator, and also detects when a delivered pulse has resulted in capture. Block 60 also determines threshold, and is connected to memory 62, where data relating to steering parameters are stored. Parameter data are generated internally as a function of the threshold detection or are received from an external programmer. As a result of the parameter data and timing determined at block 60, data for pulse parameter and timing control are coupled to block 64. A closed loop system for controlling the pulse parameters of the delivered stimulus pulses is thus provided.

Figure 3A:
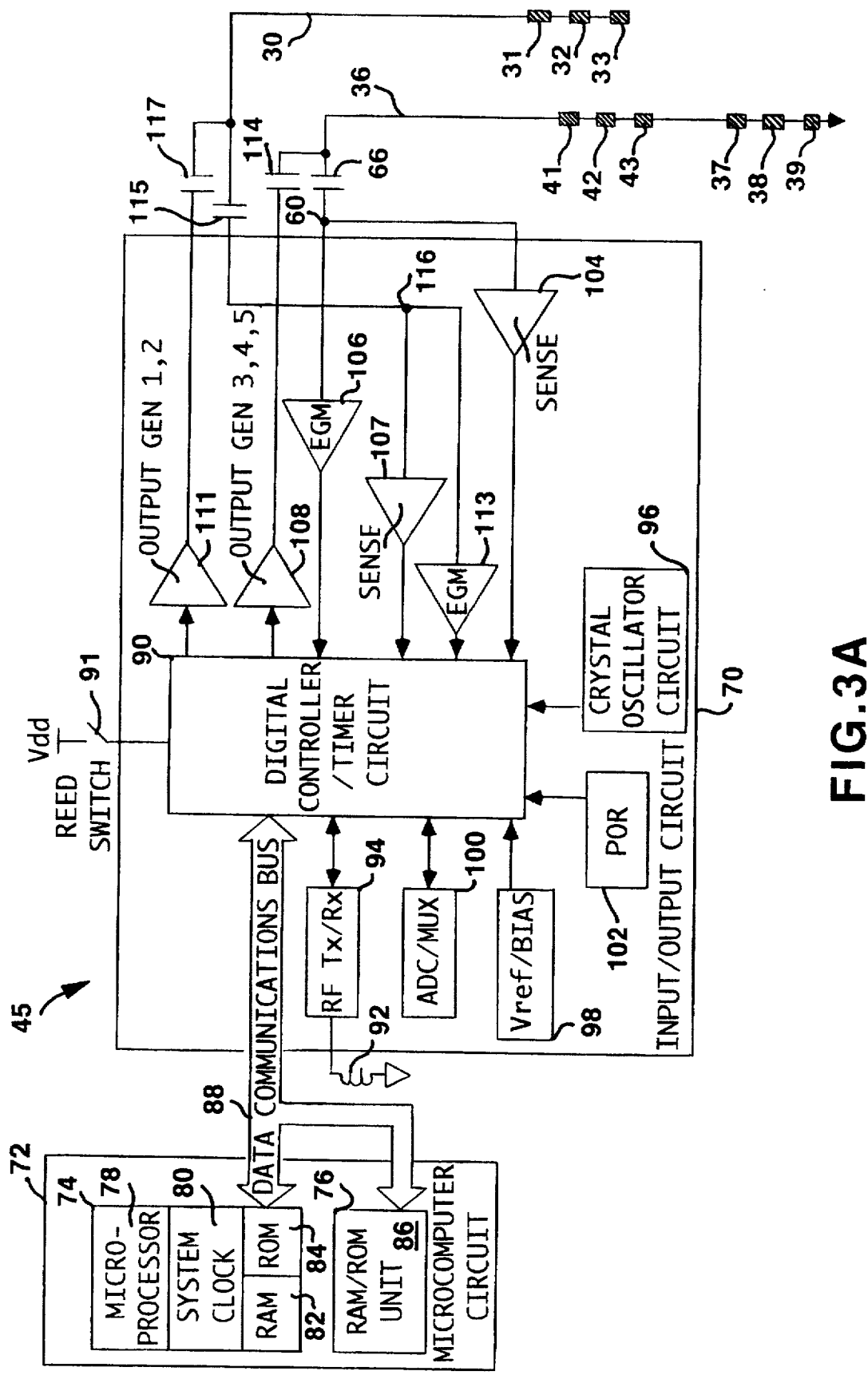
FIG. 3A shows a block diagram of a pacing system of the present invention that provides stimulus pulses steered to a patient's left atrium and other cardiac sites as part of a multi-chamber pacing system.
Figure 3B:
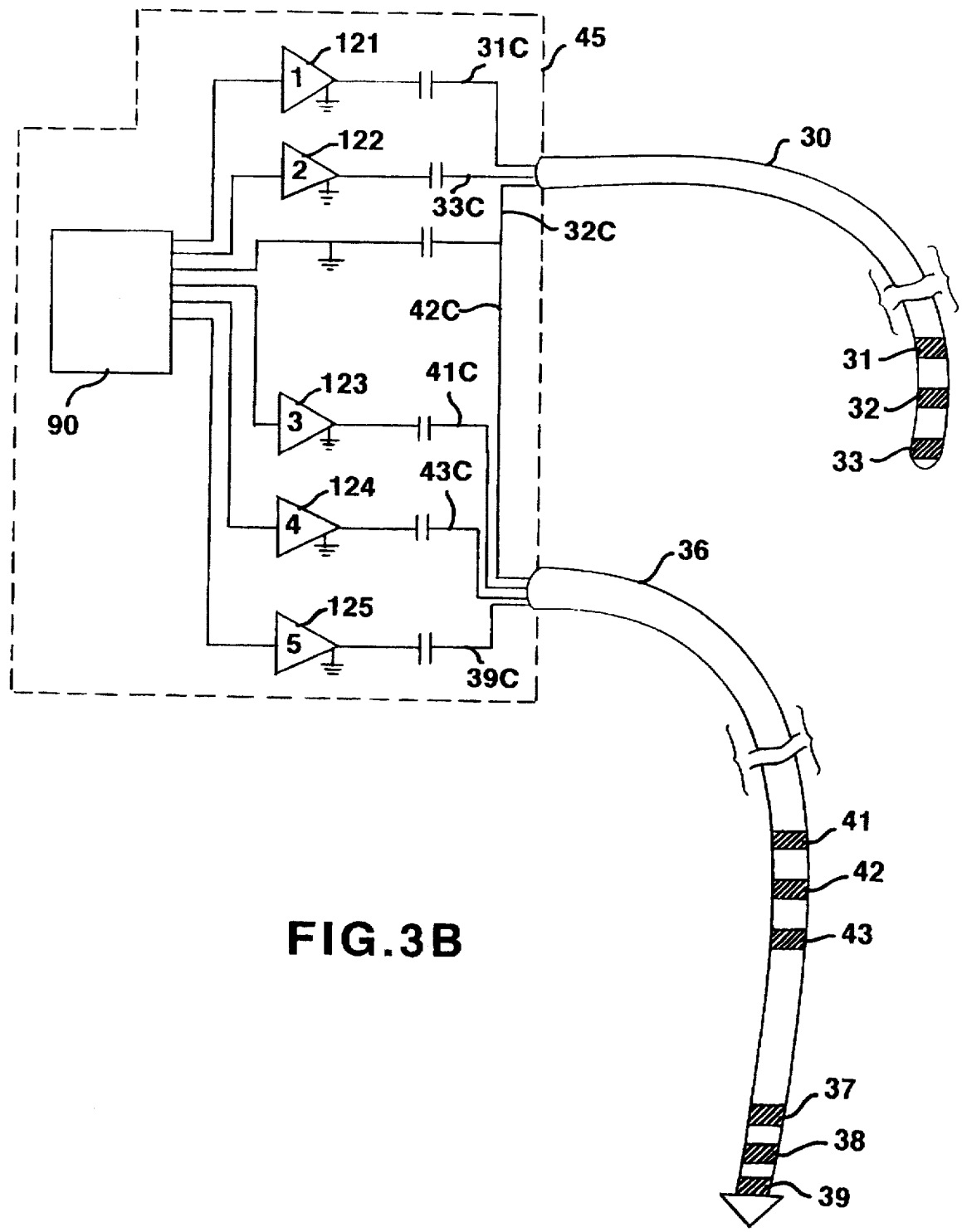
FIG. 3B shows a block diagram of the present invention, where details of the output generator portion of the system of FIG. 3A are shown.
Figure 3C:
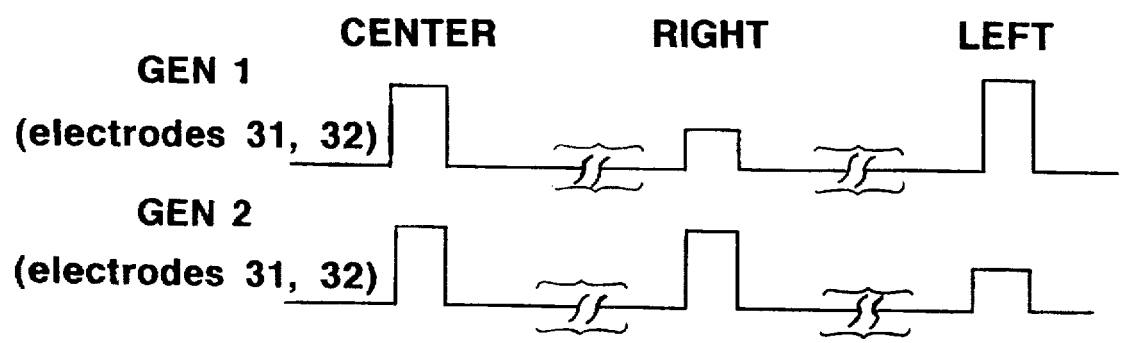
FIG. 3C shows a timing diagram illustrating variations in the amplitude components of the individual pulses forming the composite pulse of the system of FIG. 3A, where those variations cause steering of the composite pulse to different atrial locations.

FIGS. 3A, 3B and 3C show a multichamber pacemaker having the steering feature of the present invention, where the left atrium, right atrium, or the right ventricle, or any combination of those chambers, may be paced with steered pulses. FIG. 3A is modified in respect of FIG. 2 in U.S. Pat. No. 5,441,525, the entirety of which is hereby incorporated by reference herein. Although the present invention is described in accordance with a microprocessor-based architecture, it will be understood by those of ordinary the skill in the art that it may be implemented using other technology such as digital logic-based, custom integrated (IC) architecture, or with any other combination of hardware and software familiar to those of ordinary skill in the art.

FIG. 3A shows pacemaker or stimulator 45 modified in respect of a conventional DDD pacemaker to provide multiple generators (GEN 1,2 and GEN 3,4,5) for generating a plurality of component composite steering pulses for pacing the left atrium, the right atrium or the right ventricle. Generators 1 and 2, shown jointly at 111, have their outputs coupled through at least one capacitor 117 to lead 30 for delivering pulse components between electrode pairs 31,32 (common) and 33,32. The parameters of each pulse component are adjusted to accurately steer the composite pulse so that the left atrium is captured. Generators 3 and 4 (shown at 108) likewise have their outputs connected to lead 36 for delivering steered pulses to the right atrium across electrode pairs 41,42 and 43,42. Generator 5 (also shown at 108) is connected to distal electrode 39 or electrode 37 for unipolar pacing of the right ventricle, or between active electrode 39 and common electrode 38, active electrode 37 and common electrode 38, or between active electrodes 37 and 39 and .common electrode 38 for bipolar pacing. Note that electrode 37 need not be used or even present in lead 36 if tip electrode 39 is in contact with and engages cardiac tissue. Furthermore, common electrode 38 need not be used or even present if case 35 is used as a common electrode in the unipolar pacing case.

Input/Output circuit 70 contains the input and output analog circuits and digital controlling and timing circuits necessary for the detection of electrical signals originating in the heart and sensed by sensors (not shown) connected to leads 30 and 36. Input/output circuit 70 further contains the circuitry required for the application of steered stimulating pulses to the heart under the control of software-implemented algorithms in Microcomputer Circuit 72.

Microcomputer Circuit 72 comprises an On-Board Circuit 74 and an Off-Board Circuit 76. On-Board-Circuit 74 includes microprocessor 78, system clock 80, and on-board RAM 82 and ROM 84. Off-Board Circuit 76 includes off-board RAM/ROM Unit 86. Microcomputer Circuit 72 is coupled by Data Communication Bus 88 to Digital Controller/Timer Circuit 90. Microcomputer Circuit 72 may be fabricated of custom IC devices and augmented by standard RAM/ROM components. It will be understood by those skilled in the art that the electrical components represented in FIG. 3A are powered by an appropriate implantable-grade battery power source that is not shown explicitly.

Antenna 92 is connected to Input/Output Circuit 70 for uplink/downlink telemetry through radio frequency (RF) Transmitter/Receiver Circuit (RF TX/RX) 94. Telemetry of both analog and digital data between antenna 92 and an external device such as an external programmer (not shown) is accomplished in a preferred embodiment of the present invention by first digitally encoding all data and then pulse position modulating those data on a damped RF carrier. U.S. Pat. No. 5,127,404 entitled "Telemetry Format for Implantable Medical Device," incorporated herein by reference in its entirety, describes such a telemetry system. Reed switch 91 is connected to Input/Output Circuit 70 to enable patient follow-up through telemetry and programming functions.

Crystal Oscillator Circuit 96 (typically a 32,768 Hz crystal-controlled oscillator) provides main timing clock signals to Digital Controller/Timer Circuit 90. Vref/Bias Circuit 98 generates a stable voltage reference and bias currents for the analog circuits of Input/Output Circuit 70. ADC/Multiplexer Circuit (ADC/MUX) 100 digitizes analog signals and voltages to provide telemetry and a replacement time-indicating signal or end-of-life function (EOL). Power-On-Reset Circuit (POR) 102 functions to initialize pacemaker 40 with programmed values during power-up, and reset the program values to default states upon the detection of a low battery condition, or in the presence of certain undesirable conditions such as unacceptably high electromagnetic interference (EMI).

Operating commands for controlling the timing of pacemaker 45 in FIG. 3A are coupled by bus 88 to Digital Controller/Timer Circuit 90, where digital timers set the overall escape interval of the pacemaker and the various refractory, blanking and other timing windows for controlling the operation of peripheral components in Input/Output Circuit 90.

Digital Controller/Timer Circuit 90 is coupled to sense amplifiers (SENSE) 104 and 107 and to electrogram (EGM) amplifiers 106 and 1 13 for receiving amplified and processed signals representative of the electrical activity of the patient's ventricle and atrium, respectively. Those signals are sensed by one or more electrodes 31, 32, 33, 37, 38, 39, 41, 42, 43, depending on which cardiac sites are being paced.

Although only two sense amplifiers are shown in FIG. 3A, a plurality of sense amplifiers and a switching matrix may also be employed, as, for example, shown in FIG. 2 at 50 and at 52,53,54. See also U.S. Pat. No. 5,423,873, incorporated herein by reference in its entirety, where a switching arrangement for switching pacemaker output and input terminals to different electrodes in a multi-electrode arrangement is disclosed.

SENSE amplifiers 104 and 107 produce sense event signals for resetting the escape interval timer within Circuit 90. The electrogram signal provided by EGM amplifier 106 may be used when the implanted device is being interrogated by the external programmer/transceiver (not shown) to transmit by uplink telemetry a representation of the analog electrogram of the patient's electrical heart activity. See, for example, U.S. Pat. No. 4,556,063 to Thompson et al., entitled "Telemetry System for a Medical Device," incorporated herein by reference in its entirety.

The plurality of output pulse generators represented at 108 and 111 provide pacing stimuli to the patient's heart through output capacitors 114 and 117 and leads 30 and 36 in response to pacing trigger signals output by Digital Controller/Timer Circuit 90 each time an escape interval times out, an externally transmitted pacing command is received, or in response to other stored commands. As discussed above, each delivered pulse is, in fact, a composite of a plurality of individual component pulses, where each individual component pulse has a particular programmed or adjusted set of amplitude, duration (width) and phase parameters corresponding to it.

FIGS. 3B and 3C show a more detailed embodiment of the present invention for generating and steering pulses. In FIG. 3B, generators 1–5 are controlled by control circuit 90 in respect of timing and amplitude, duration and phase parameters. Generator 1 at 121 is coupled through capacitor C1 to lead conductor 31 C connected to the output through lead 30 to electrode 31. The output of generator 2 at 122 is coupled through capacitor C2 on conductor 33C to electrode 33. The pacemaker ground or common is connected through capacitor CC on conductor 32C to electrode 32. Pulse parameter control circuit 90 determines the direction the composite pulse will have when it is delivered to the left atrium, as illustrated in FIG. 3C.

Thus, for a centrally directed pulse the amplitudes across pairs 31,32 and 33,32 are substantially equal. For a right-directed pulse the amplitude across electrodes 33,32 is greater than that across electrodes 31,32. For a left-directed pulse the relative amplitudes are switched so that the pulse originating in generator 1 and delivered across electrodes 31,32 has a greater amplitude than that delivered across electrode 33,32. Output pulse parameters may be adjusted by standard threshold determination techniques and optimized parameters stored in memory.

Pulses delivered by lead 36 are generated by generators 123, 124 and 125 and coupled through capacitor C3 and conductor 41 C, capacitor C4 and conductor 43C, and capacitor C5 and conductor 39C, respectively, to electrodes 41,43 and 39. While not shown specifically, pulses generated and delivered across electrode pairs 41,42 and 43,42 are likewise adjusted in amplitude or duration, or both amplitude and duration to optimize pacing of the right atrium from those floating electrodes. Since the distal end of lead 36 may be anchored in the apex of the right electrode, there is no need to generate composite steering pulses for delivery to electrodes 39,38. Of course, atrial and ventricular pace pulses are controlled in respect of the time sequence in which they are delivered (as in a conventional DDD pacemaker).

Figure 3D:
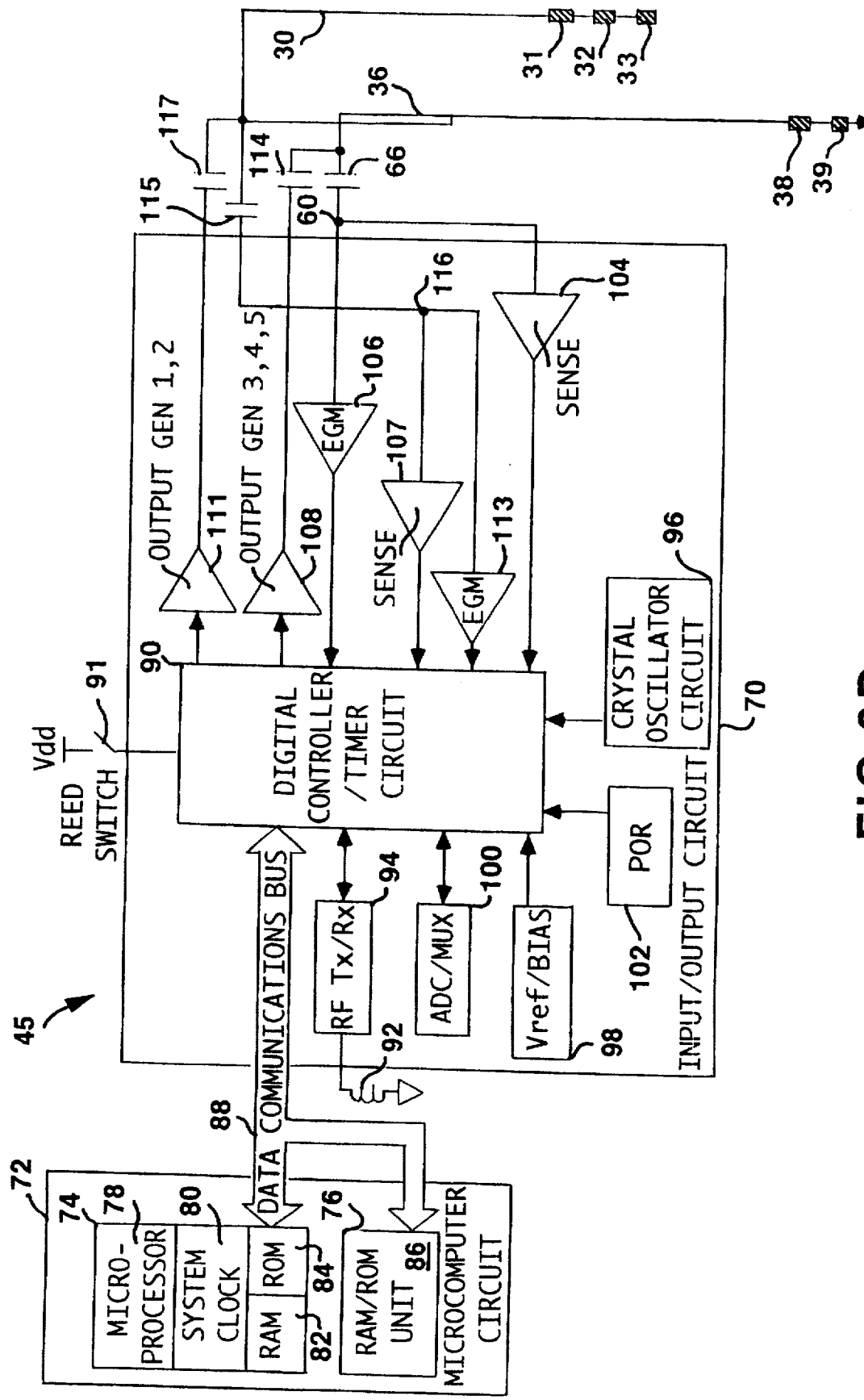
FIG. 3D shows a block diagram of the pacing system shown in FIG. 1(c) that provides pacing pulses steered to two, three or four chambers of a patient's heart as part of a multi-chamber pacing system.

FIG. 3D shows a block diagram of the pacing system shown in FIG. 1(c) that provides pacing pulses steered to one, two, three or four chambers of a patient's heart as part of a multi-chamber pacing system.

Figure 3E:
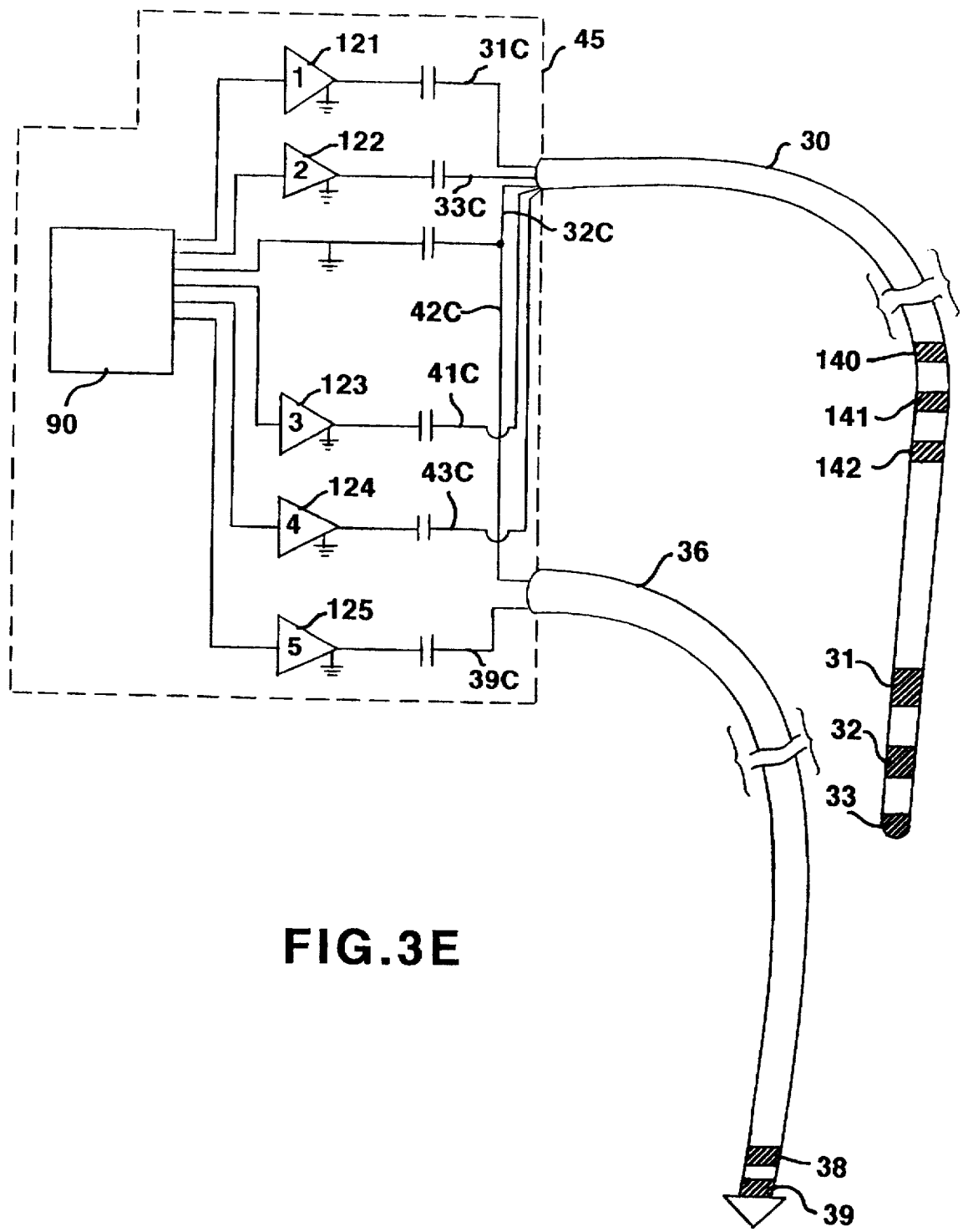
FIG. 3E shows a block diagram of the present invention, where details of the output generator portion of the system of FIG. 3C are shown.

FIG. 3E shows a block diagram of the present invention, where details of the output generator portion of the system of FIG. 3C are shown.

Figure 4A:
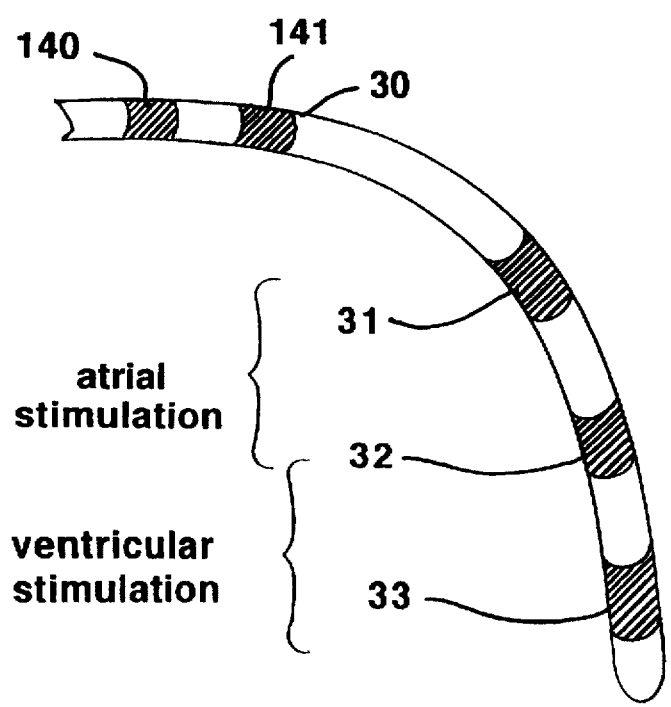
FIG. 4A shows a distal end portion of a lead of the present invention positioned proximate the heart, where the lead has plural electrodes for delivery of respective pacing pulses steered to different cardiac sites.

We refer now to FIGS. 4A through 4E which illustrate an embodiment of the present invention for multi-site pacing from a single lead. We also refer now to pacemaker or stimulator 45 in FIGS. 3A and 3B, and U.S. Pat. 5,265,601, incorporated herein by reference in its entirety. As illustrated in FIG. 4A, the distal end portion of lead 30 is positioned in the coronary sinus or deep cardiac vein, and is connected to pacemaker 45. For pacing in both the atrium and the ventricle, electrode pair 31,32 delivers atrial pacing pulses, while pair 33,32 delivers ventricular pacing pulses. Individual pulse components are preferably generated by generators 121 and 122 (as shown in FIG. 3B) and are controlled appropriately in respect of amplitude, width and phase.

Figure 4B:
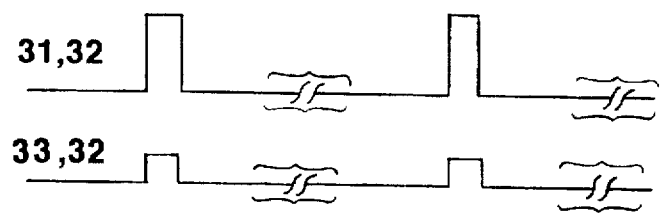
FIG. 4B shows a timing diagram illustrating the delivery of one composite steered pulse per cardiac cycle.
Figure 4C:
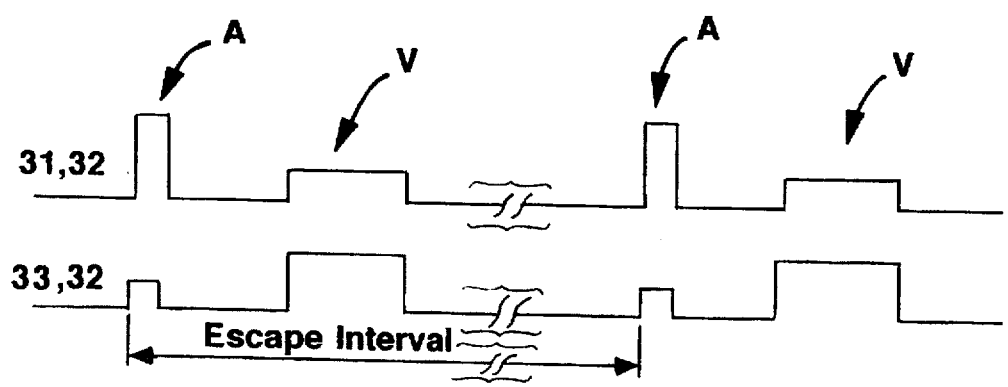
FIG. 4C shows a timing diagram illustrating the delivery of two composite steered pulses per cardiac cycle.
Figure 4D:
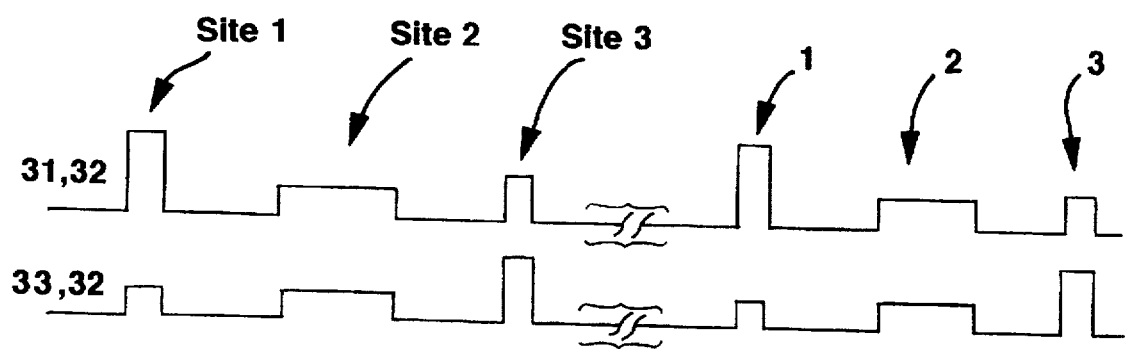
FIG. 4D shows a timing diagram illustrating the delivery of three composite steered pulses per cardiac cycle.

As shown in FIGS. 4B, 4C and 4D, pacing of one, two or more cardiac sites is possible with the present invention. FIG. 4B shows a single composite pulse being generated for each cycle, and may be employed to pace the left or right atrium. Steering is accomplished by adjusting the relative magnitudes of the component pace pulses. For example, the magnitude of the signal delivered across electrode pair 31,32 may exceed that delivered across electrode pair 33,32.

FIG. 4C illustrates a pulse train for pacing two cardiac sites for each cycle, and may be employed to pace the atrium and ventricle separately. For example, the first pulse components may have unequal amplitudes, phases or widths, resulting in steering of the resulting electrical field in a first direction; the second pulse components may have equal amplitudes, phases or widths, resulting in a straight-ahead field pattern.

For combined atrial and ventricular pacing, composite atrial stimulating pulses may be of relatively low magnitude so that the ventricle is not stimulated. Likewise, composite ventricular pulses may be of relatively high magnitude but may be delivered during the heart's natural refractory period so that only ventricular stimulation results. The atrial sense amplifier (or amplifiers) may be adjusted to have a lower threshold for sensing than the ventricular amplifier, so that lower-magnitude atrial signals exceed only the threshold of the atrial amplifiers, while higher-magnitude ventricular signals exceed the threshold of both amplifiers and may thus be recognized with appropriate logic. See, for example, U.S. Pat. No. 5,265,601.

FIG. 4D illustrates a waveform for stimulating three sites, where for each cardiac cycle three different composite pulses are generated and delivered across electrode pairs 31,32 and 33,32. In accordance with this embodiment of the present invention, a third composite pulse may be delivered that has a greater voltage across electrode pair 33,32 than it does across electrode pair 31,32, resulting in the first and third composite pulses being steered in different directions. Note that steering may be aided or effected by changing slightly the phase or width of the individual component pulses respecting other individual component pulses.

Figure 4E:
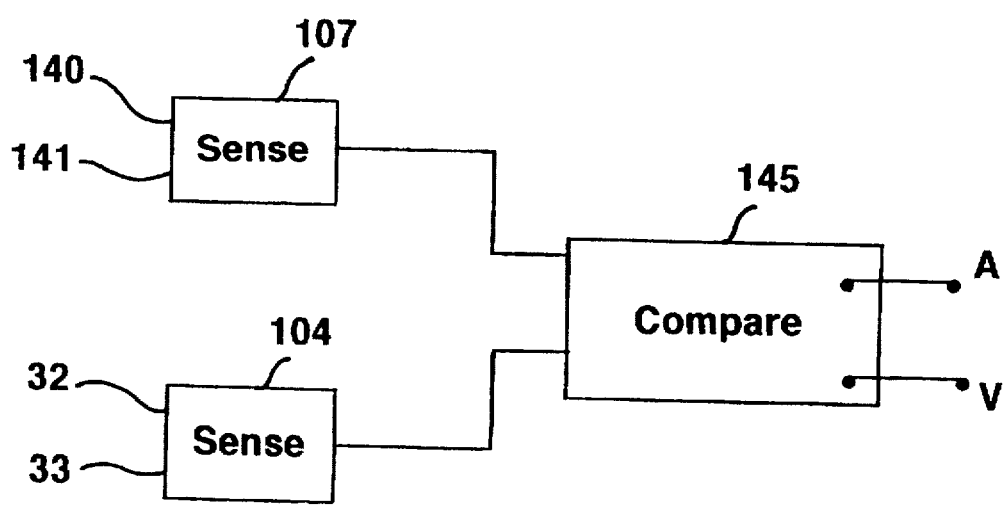
FIG. 4E shows a block diagram of a system modification for detecting the origin of a sensed signal and to provide enhanced discrimination of sensed atrial and ventricular signals.

FIGS. 4A and 4E show an embodiment of the present invention where the capability of a single lead system to discriminate between sensed signals originating in the atrium and the ventricle is enhanced, permitting better and more reliable pacemaker operation. Lead 30 has a pair of sense electrodes 140,141 positioned proximal to the distal electrodes. When lead 30 is implanted the electrodes are positioned close to the atrium. Due to this relative positioning, a signal originating in the atrium is detected at electrode pair 140,141 before it is detected at electrode pair 32,33. Likewise, a signal originating in the ventricle is detected at electrode pair 32,33 before it propagates to electrode pair 140,141.

As shown in FIG. 4E, the signals from the two electrode pairs are sensed at electrode pair 104,107 and time-compared at compare block 145. Such a comparison may be accomplished by simply detecting the leading edge of the incoming signal and setting a flip-flop to output signal A for a signal of atrial origin and to output signal V for a signal of ventricular origin. Alternatively, a Doppler detector and signal processor may determine the location from which a sensed signal has originated. Such a Doppler detector may be employed instead of or in addition to electrode pair 140,141 for sensing pressure waves resulting from a cardiac chamber contraction.

In cardiac pacing applications, the amplitude of each pulse component is preferably varied in about 0.5 Volt increments through a range of about 0.5 to about 7.5 Volts; pulse widths are preferably varied in about 0.03 ms increments through a range of about 0.03 to about 1.5 ms; phase delays of one pulse relative to another are preferably varied in about 0.03 ms increments over a range of about −1.0 to about +1.0 ms. Amplitude variations for defibrillation are much greater. Amplitude components may be varied in about 25 or about 50 Volt increments over a range between about 25 Volts and 750 Volts.

Figure 5:
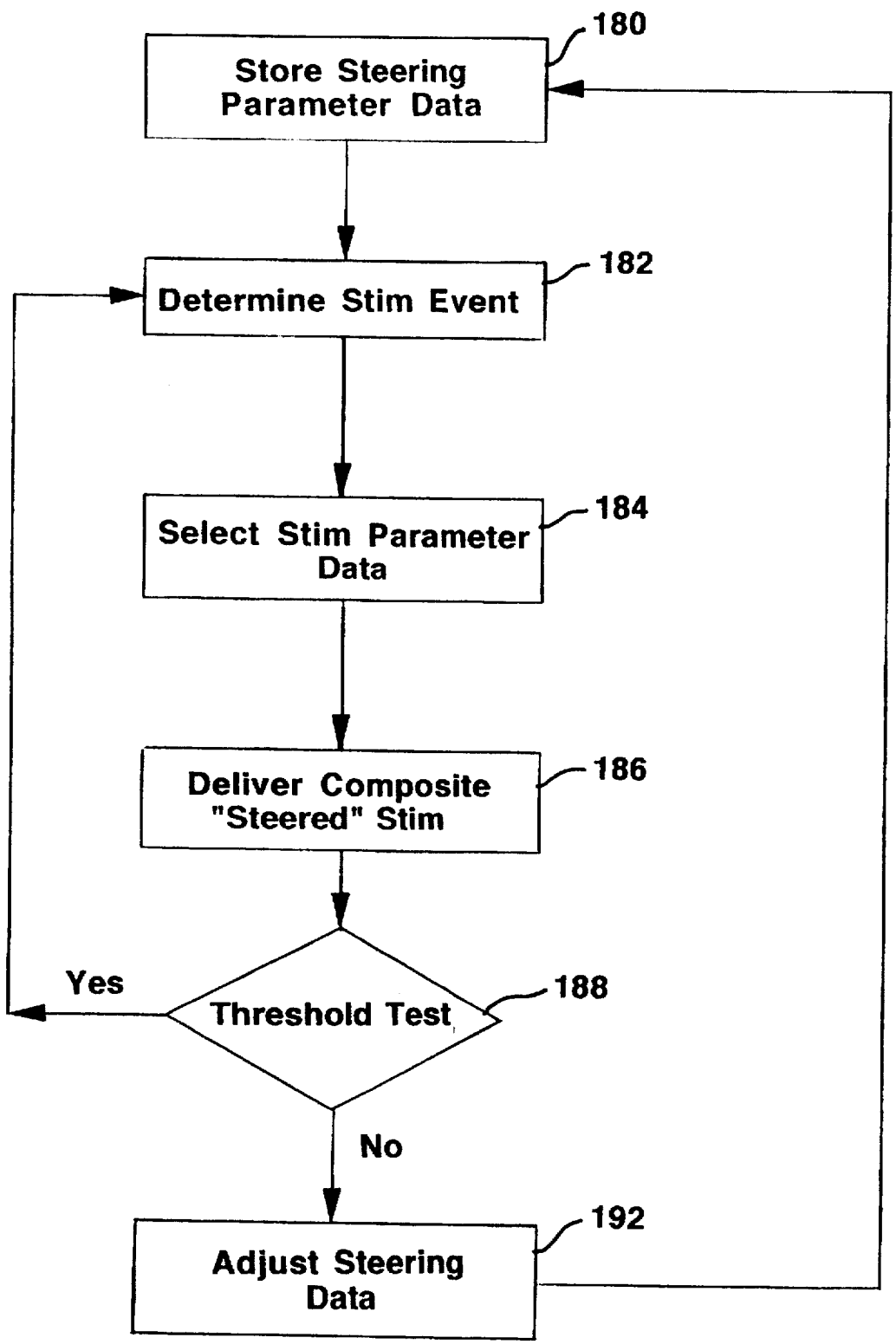
FIG. 5 shows a flow diagram of a routine of the present invention for carrying out a closed loop adjustment of steering parameters.

FIG. 5 presents a simplified, generic flow diagram of the primary steps involved in practicing one embodiment of present invention. Steering, or pulse component parameter, data are stored in the pacemaker at 180. Such data may be acquired initially by external programming or generated automatically by threshold testing. This embodiment of the present invention may be capable of delivering types of pulses such as pacing or defibrillation pulse, ventricular or atrial pulses, left or right atrial pulses, left or right ventricular pulses, and the like. A determination is made at 182 concerning which type of pulse is to be delivered. After the type of stimulus is determined, appropriate parameter data for individual pulse components are determined at 184 for the steered pulse that will be delivered. The resulting composite pulse comprising a plurality of synchronously or near-synchronously generated individual component pulses is delivered at 186. A threshold test is performed at 188 to determine whether or not capture has occurred. The pulse delivered at 186 is also compared with a stored threshold pulse at 188. Steering parameters may be adjusted at 190 according to the results of the threshold test made at 188. If a steering parameter adjustment is made, one of more individual pulse component parameters are adjusted at 192.

Figure 6A:
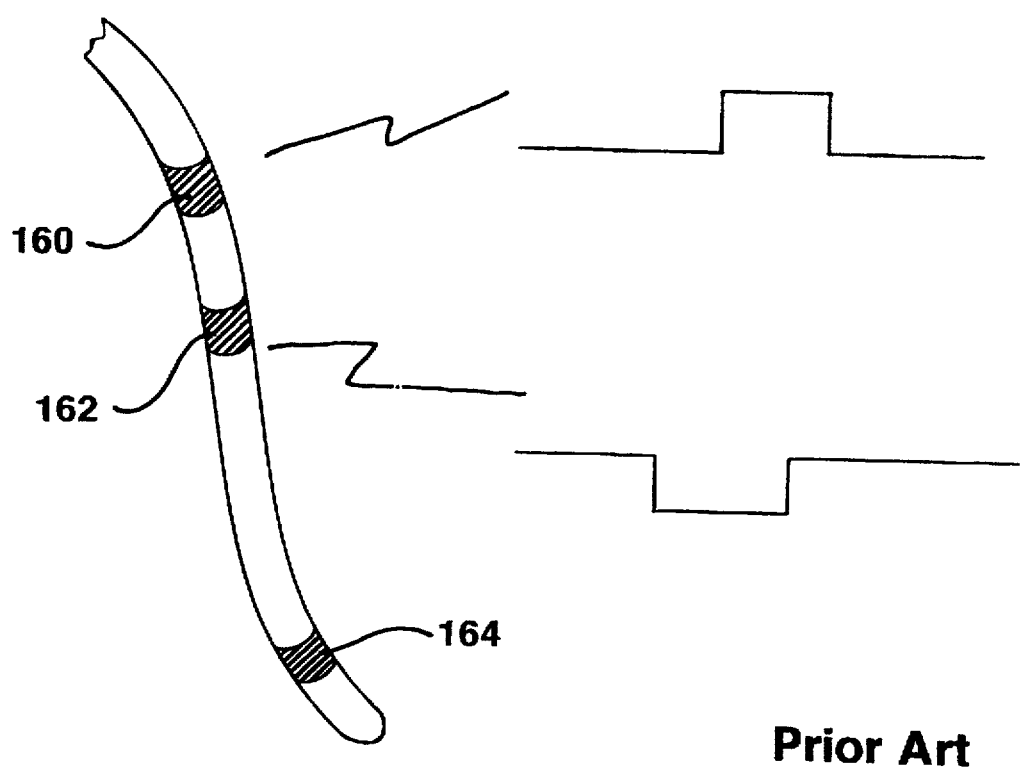
FIG. 6A shows a sketch of a distal portion of a typical prior art single pass lead used for delivering omnidirectional bi-phasic stimulus pulses from a floating atrial electrode.

It is known to pace the atrium using a pair of floating electrodes disposed in the atrium. When such a method is employed successfully, effective DDD pacing results using only one floating lead. FIG. 6A shows a prior art single pass lead having two floating atrial electrodes 160 and 162, and one or two electrodes 164 disposed at or near the distal tip of the lead for ventricular pacing and sensing. Using such a configuration, it is known to deliver two opposite phase overlapping pulses to provide a composite biphasic pulse. Each pulse of those pulses is delivered between electrode 160 or 162 and the pacemaker can, or alternatively between electrode 160 and 162. However, biphasic pulses so delivered are omnidirectional only. According to conventional methods, the magnitude of the resulting biphasic pulse may be adjusted while attempting to achieve capture.

Contrariwise, and in lieu of or in addition to merely increasing the magnitude of the delivered pulse to cause capture, in the present invention atrial or ventricular pacing pulses may be steered over a range of cardiac sites using various orientations and directions until an optimum cardiac site or orientation for capturing the atrium is discovered. For example, FIGS. 3A and 3B illustrate circuitry, leads and electrodes of the present invention that may be combined to form an improved pacemaker system utilizing a conventional VDD pacemaker and steering electrodes, where a single pass lead 36 is employed. The resulting pacing system is a single pass DDD pacing system embodiment of the present invention similar in some respects to known VDD systems using floating electrodes, but having the additional, significant advantage of delivering pacing pulses that are steered in an optimum direction or to an optimum cardiac site.

Figure 6B:
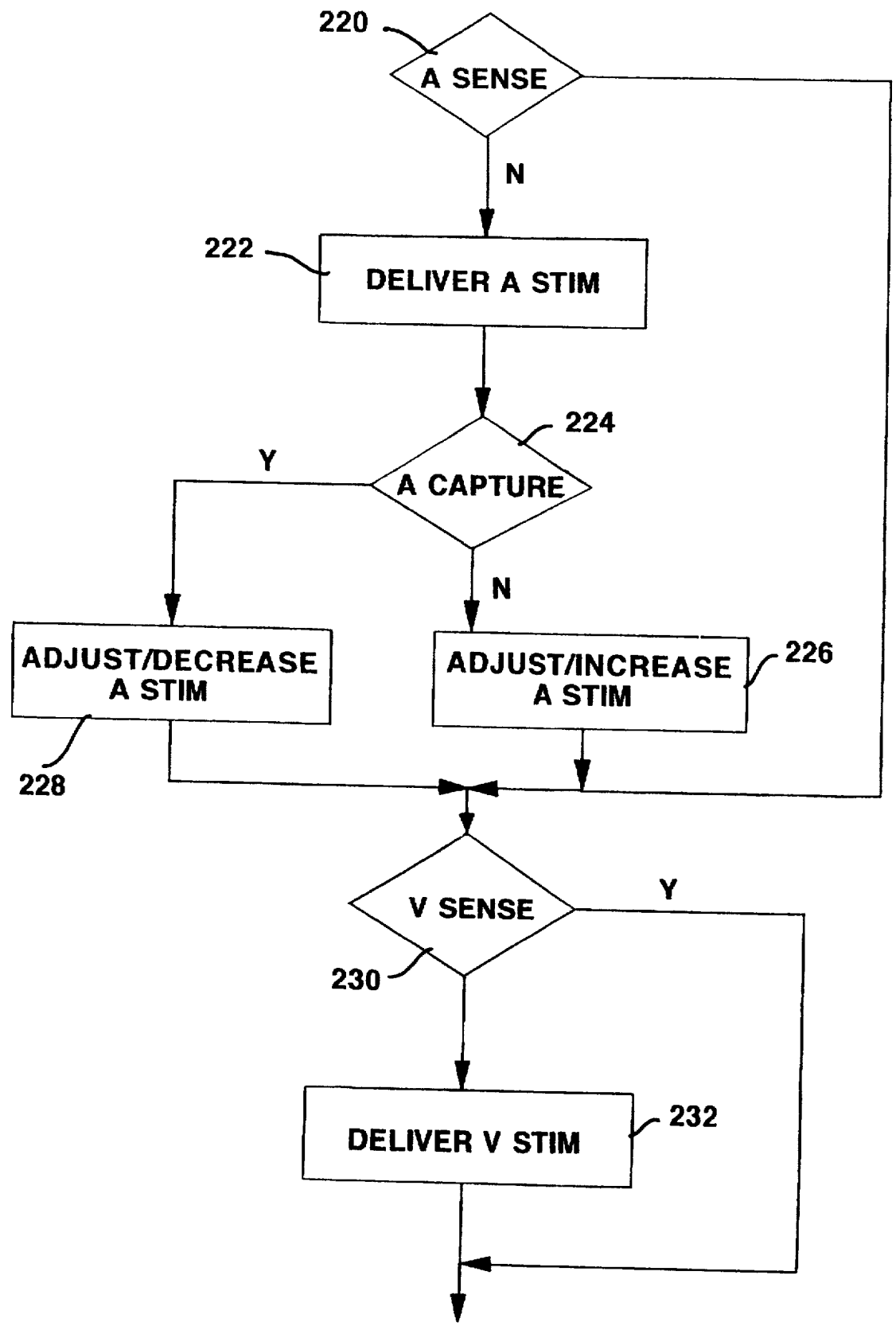
FIG. 6B shows a flow diagram of a routine for the present invention for providing closed loop adjustment of steering parameters for use with the lead of FIG. 6A.

FIG. 6B shows a flow diagram for executing the steps of a closed loop system for assuring capture in a DDD pacing system having a single pass lead, where pulses are steered in accordance with the present invention. At 220 it is determined whether or not an atrial signal is sensed during an atrial escape interval having a first predetermined length. If an atrial signal is sensed during that interval and the delivery of an atrial stimulus is therefore not required, the method requires stepping to 230, where it is determined whether or not a ventricular signal is sensed within a ventricular escape interval having a second predetermined length.

If no atrial signal is sensed within the atrial escape interval, the method requires stepping to 222 and delivering an atrial stimulus steered for optimum capture. At 224 it is determined whether or not atrial capture occurred. If such capture has occurred, one or more individual atrial pulse parameters may be modified at 228 to decrease the stimulus delivered to the atrial site. If such capture has not occurred, then one or more individual atrial pulse parameters may be modified to change the direction or orientation in which the composite pulse is steered. Alternatively, the magnitude of the composite pulse may simply be increased.

At 230 the pacemaker waits to see if a sensed ventricular signal occurs before the end of the ventricular escape interval. If such a signal does occur within the ventricular escape interval, the method is terminated ends and the entire process begins anew at 220. If no such ventricular signal occurs within the ventricular escape interval, then a ventricular stimulus is delivered. Although not shown explicitly in FIG. 6B, the method of the present invention may include having the pacemaker step through a capture detection routine and corresponding threshold adjustment for ventricular pulses in a manner similar to that described above for atrial pulses.

Figure 7A:
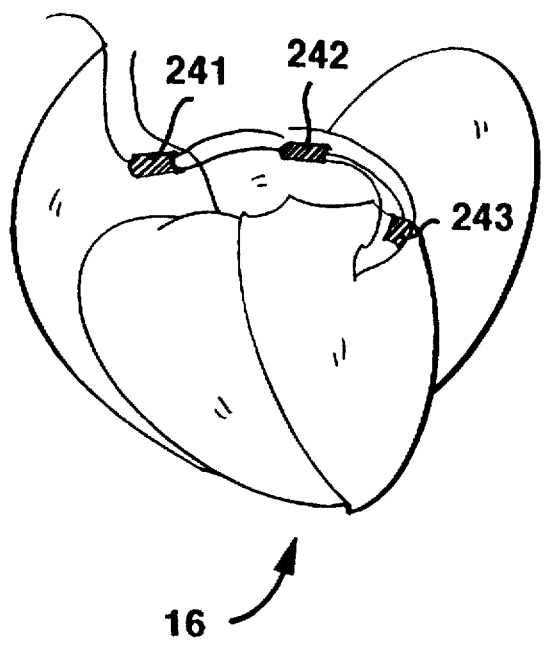
FIG. 7A shows a perspective diagram of a lead of the present invention having electrodes positioned to apply a steered atrial defibrillation or cardioversion stimulus to the atrium.
Figure 7B:
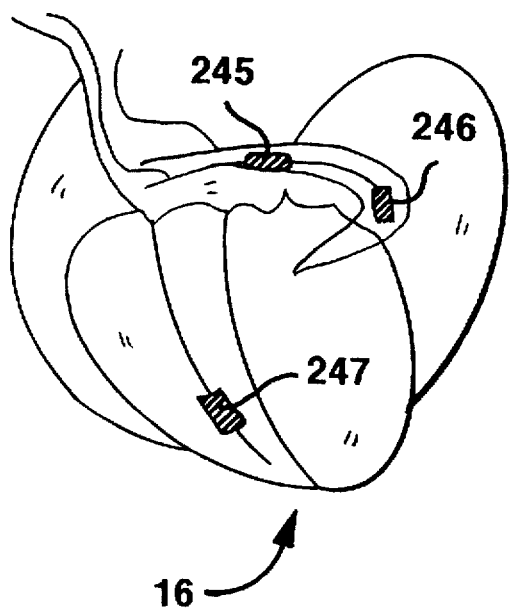
FIG. 7B shows a perspective view of a pair of leads of the present invention having electrodes positioned to apply a steered ventricular defibrillation or cardioversion stimulus to the ventricle.
Figure 7C:
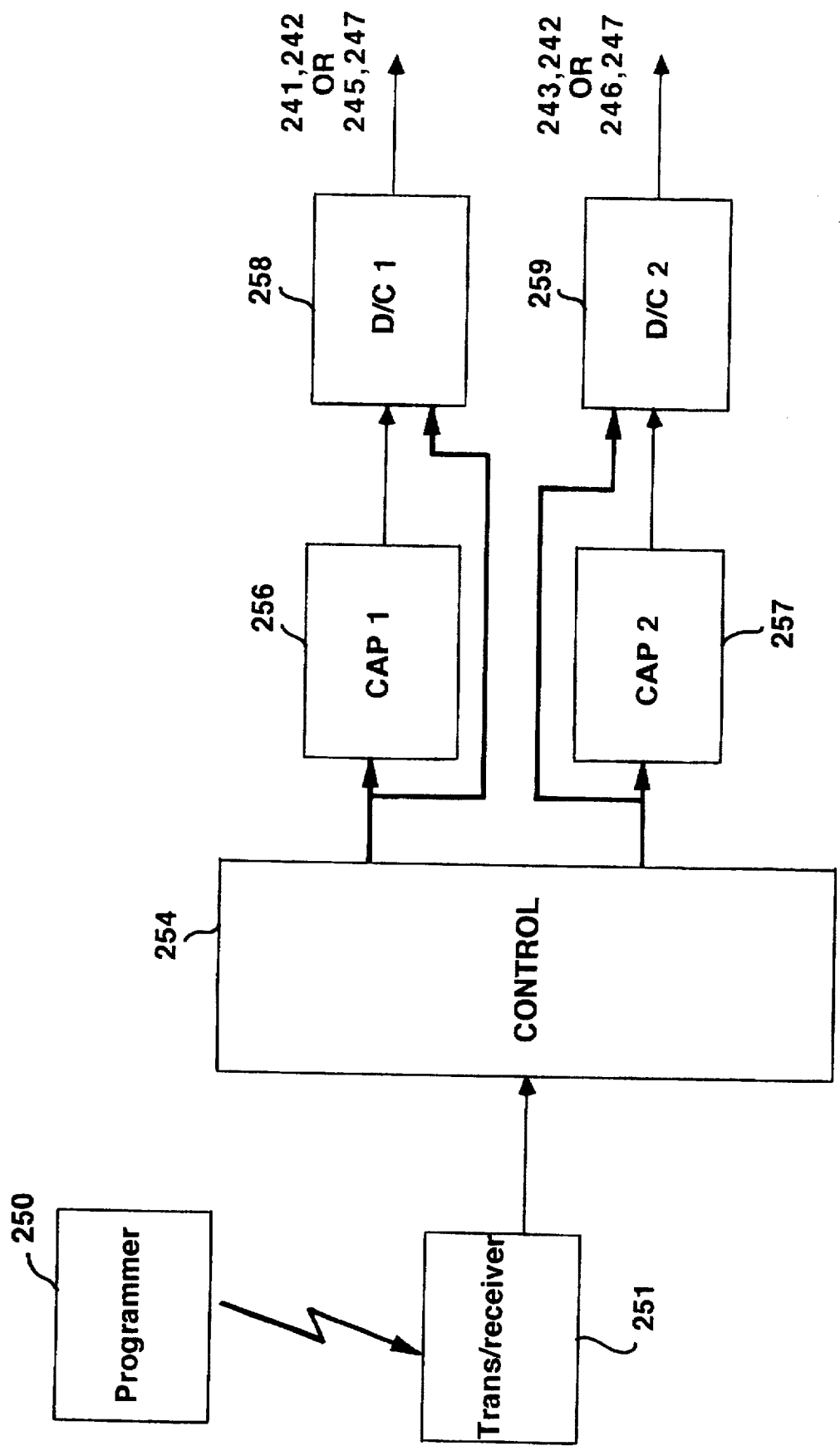
FIG. 7C shows a block diagram of the primary components of a system for the present invention for delivering a steered defibrillation or cardioversion stimulus to the electrodes of FIG. 7A or 7B.

FIGS. 7A, 7B and 7C illustrate additional embodiments of the present invention for preventing defibrillation and arrhythmia. Atrial defibrillators are well known and are typically employed in patients prone to atrial defibrillation. U.S. Pat. No. 5,269,298, hereby incorporated by reference in its entirety, discloses an example of such an atrial defibrillation system.

A major problem respecting known defibrillators is the pain resulting from the shocks they apply. Those shocks may have energies ranging anywhere from 2 to 35 joules. A lead typically used for atrial defibrillator applications is a coronary sinus lead, similar to lead 30 illustrated in FIG. 1, but having electrodes adapted to deliver large defibrillation pulses.

Lead dislodgment is a relatively common problem in implanted defibrillators. Small shifts in defibrillation electrode position may result in a lead having to be repositioned by surgical intervention, or in reprogramming the defibrillator to deliver increased energy pulses. Surgical intervention to reposition a lead increases patient discomfort and the risk of infection, and also increases health care costs. Reprogramming a defibrillator to deliver increased amplitude pulses increases the degree of pain a patient experiences when a shock is delivered and also increases patient anxiety owing to heightened anticipation of the delivery of the next defibrillation shock.

FIG. 7A shows an embodiment of the present invention where a lead has three electrodes 241, 242, and 243 positioned in the coronary sinus, the lead having a certain initial orientation and configuration following implantation. The threshold is initially optimized by adjusting the individual component pulse parameters corresponding to electrode pairs 241,242 and 243,242. The resulting composite pulse is preferably steered to permit optimum chronic delivery of defibrillation pulses. The defibrillator may also be programmed to deliver steered defibrillating stimuli which stimulate the atrium only, contrary to known systems that require defibrillating pulses to be delivered in overlapping or closely timed fashion to prevent undesired stimulation of the ventricle.

If the lead shifts position over time, and as a result stimulation efficiency decreases, the present invention permits individual pulse parameters to be re-programmed so that the composite defibrillation pulse is once again delivered with optimum efficiency and positional accuracy. In another embodiment of the present invention, the defibrillator may re-program itself by modifying individual pulse parameters on a periodic or on-going, continual basis so that optimum delivery of defibrillation pulses is maintained, even though the lead shifts position.

FIG. 7C shows a modified portion of the defibrillator circuit shown in the figure of U.S. Pat. No. 5,269,298, where the circuit described and shown therein is configured for use in the present invention. FIG. 7C shows a programmer 250 that preferably communicates by telemetric means with transmitter/receiver 251. Programmer 250 reprograms and downloads parameter data for each individual pulse component that is to be delivered by the defibrillator, and causes the defibrillator to steer a composite pulse having a certain desired amplitude to a desired cardiac site. Parameter data corresponding to the individual pulse components are downloaded to control 254 via transmitter/receiver 251. Control circuit 254 controls the delivery of individual pulse components that conform to the various phase, width and amplitude parameters downloaded from programmer 250.

Control circuit 254 controls the charge and discharge of first capacitor 256 through output circuit 258. For example, control circuit 254 may determine different or equal charges each capacitor will hold to effect steering. Alternatively, control circuit 254 may determine equal or different durations of time over which each capacitor discharges to effect steering. Output circuit 258 delivers a first individual pulse component across electrode pair 241,242. Control circuit 254 likewise controls the charge and discharge of second capacitor 257 through output circuit 259. Output circuit 259 delivers a second individual pulse component across electrode pair 243,242. The combined outputs of output circuits 258 and 259 result in a delivered composite pulse that may, according to the relative amplitudes, phases and widths of its component individual pulses, be steered in a desired direction or orientation to stimulate a desired cardiac site.

FIGS. 7B and 7C illustrate a two lead system of the present invention for delivering defibrillation pulses to the ventricle, where pulses are steered to shock the ventricle only. A first lead having a pair of electrodes 245,246 is positioned in the coronary sinus. A second lead having a common or indifferent electrode 247 and a standard RV pacing and sensing electrode 248 is positioned in the ventricle. In this embodiment of the present invention, steered pulses are delivered between the first lead and the second lead across electrode pair 245,247 and electrode pair 246, 247; conventional ventricular pacing and sensing is effected across electrode pair 247,248. The amplitude, phase and width parameters corresponding to each of the two individual pulse components delivered across electrode pairs 245,247 and 246,247 are optimized to steer the composite pulse to a selected (presumably optimum) site in the ventricle. Through appropriate programming, individual pulse component parameters may subsequently be modified if one or both leads migrate after implant.

The embodiment of the present invention shown in FIGS. 1(a) through 2 may be modified to provide a system for pacing and preventing atrial arrhythmias. U.S. Pat. No. 5,403,356, incorporated herein by reference in its entirety, describes a system and method for pacing the triangle of Koch or other atrial site characterized in having a prolonged effective refractory period. The system and method disclosed in the '356 patent also prevent the occurrence of atrial tachyarrhythmias. The system disclosed in the '356 patent is modified in accordance with the present invention by implementing the methods and apparatus shown in FIGS. 7A-7C or FIG. 3B, that is by adding another output stage and providing a first lead having three electrodes.

In this embodiment of the present invention, a first lead having two active electrodes and a ground or common electrode disposed between the two active electrodes is positioned in the right atrium so that the electrodes stimulate an area of intracardiac tissue in or near the triangle of Koch. A composite pulse is emitted by the first lead, where individual pulse component parameters are adjusted to steer the composite pulse toward an optimum pacing site in or near the Triangle of Koch. A second lead, also having two active electrodes and a ground or common electrode disposed between the two active electrodes, is positioned in the right atrial appendage. A composite pulse is also emitted by the second lead, where individual pulse component parameters are adjusted to steer the composite pulse toward an optimum atrial site for arresting or preventing atrial arrhythmias.

If either of the two leads migrates after implantation, or if the threshold required for chronic stimulation changes after implantation, individual pulse component parameters may be reprogrammed and modified to account for those changes by redirecting or resteering pacing or antiarrhythmia stimuli to optimum sites. According to this embodiment of the present invention, pacing and anti-arrhythmia thresholds may be reduced to levels lower than those previously attainable because stimulation of a specific site or sites may be effected more precisely and accurately than has been possible heretofore.

U.S. Pat. No. 5,447,519, incorporated herein by reference in its entirety, describes a method and apparatus for the detection of monomorphic and polymorphic arrhythmias, and the selection of an appropriate therapy based upon that detection. In the '519 patent, morphology specific therapies are selected when the antitachyarrhythmia device is implanted. Those selected therapies are stored along with corresponding waveforms chosen on the basis of their efficacy for terminating certain tachyarrhythmias.

In another embodiment of the present invention, the selected therapies of the '519 patent are effected utilizing the steering technique of the present invention. Thus, the steering technique of the present invention is combined with the morphology selected specific therapy disclosed in the '519 patent to permit delivery of steered pulses to selected intracardiac sites. In accordance with the terminology employed in the '519 patent, in the present invention one or more of the following parameters may be adjusted to direct stimuli to selected target sites: $S_0$–$S_1$ intervals; $S_1$–$S_2$ intervals; burst length; pulse amplitude; pulse width and duration; scanning overdrive/underdrive; and the pulse, width and phase parameters of the individual component pulses that form composite cardioversion or defibrillation pulses. In this embodiment of the present invention, three or more steering electrodes are preferably employed in a manner similar to that shown in FIGS. 1 and 7A.

Figure 8:
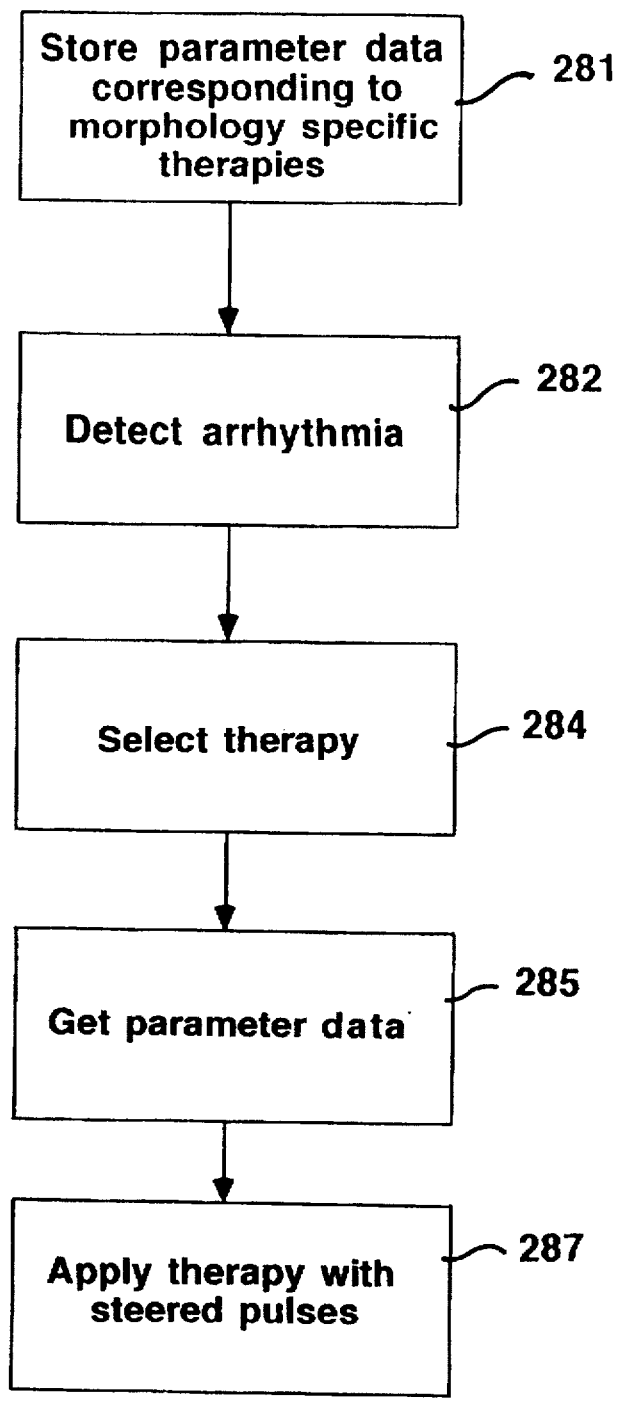
FIG. 8 shows a flow diagram of the primary steps of the present invention in a routine for applying morphology specific cardiac therapies using steered electrical stimuli.

The flow diagram of FIG. 8 shows the primary steps of a method of site specific therapy utilizing the steering techniques of the present invention. At block 281 parameter data corresponding to different morphology specific therapies are stored in the stimulator device. At block 282 an arrhythmia is detected. At block 284 an optimum therapy is selected on the basis of the characteristics of the arrhythmia detected at 282. At 285 parameter data are selected and obtained that correspond to the selected optimum therapy. Finally, the therapy is applied at 287 using steered pulses generated using the selected parameter data.

Figure 9A:
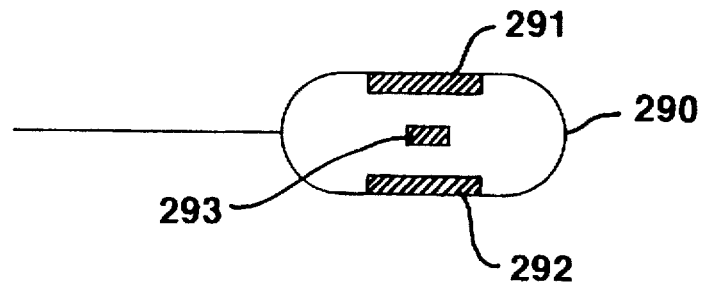
FIG. 9A shows a alternative three electrode embodiment of the present invention for applying steered pulses to one or more cardiac targets.
Figure 9B:
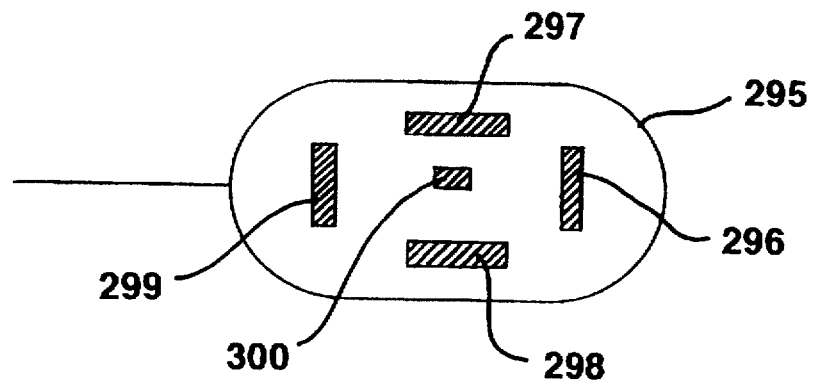
FIG. 9B shows an alternative five electrode embodiment of the present invention for applying steered pulses to one or more cardiac targets.
Figure 9C:
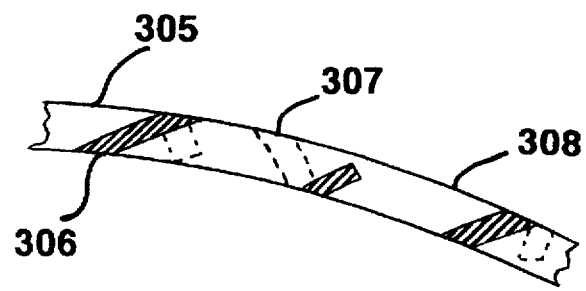
FIG. 9C shows an alternative electrode embodiment of the present invention or applying steered pulses to one or more cardiac targets, where a tubular endocardial lead is employed.

In addition to three-ring electrode configurations, the present invention includes within its scope various other electrode configurations such as those shown in FIGS. 9A, 9B and 9C. To provide steered pacing pulses according to the present invention, and regardless of the particular electrode configuration selected, the distance between active electrodes preferably exceeds about 2 centimeters. FIG. 9A shows a distal portion of a lead having two elongated peripheral electrodes 291,292 and a centrally-disposed small electrode 293. Most preferably, electrode 293 is a common cathode or ground and electrodes 291 and 292 are preferably anodes or active electrodes. Individual pulse components are delivered across electrode pairs 291,293 and 292,293. The elongated peripheral electrodes provide improved steerability and directional control characteristics respecting ring electrodes. The electrode configuration shown in FIG. 9A is most preferred when epicardial or patch-type electrodes are employed, but may also be adapted for use with transvenous leads.

FIG. 9B illustrates another electrode configuration of the present invention where four active electrodes 296, 297, 298, and 299 are employed in combination with common electrode 300 to provide various selectable combinations of electrode pairs.

FIG. 9C shows a conventional transvenous lead modified in accordance with the present invention, where at least three split ring electrodes provide enhanced composite pulse steering capability. In this embodiment of the present invention, electrodes 306, 307 and 308 are disposed on or near the distal end of lead 305. Electrodes 306 and 308 are active electrodes, while electrode 307 is a ground or common electrode. Each electrode preferably forms a portion of a spirally wound ring and has a radius spanning less than 360 degrees. The electrodes are spaced sequentially along the distal end of lead 305 and preferably do not overlap. Alternatively, the electrodes may have multiple turns, may overlap but not touch or be contiguous over some longitudinal portion of the lead, or may have a radius spanning more than 360 degrees. Common or ground electrode 307 is typically disposed between active electrodes 306 and 308. The two active electrodes may have multiple turns, while the common electrode between them may have only one or a fraction of a turn. This lead and electrode configuration of the present invention can provide increased flexibility in steering applications.

Figure 10A:
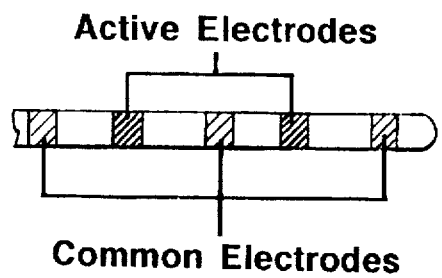
FIGS. 10(a) through 10(f) show some different embodiments of the lead and electrode sets of the present invention for applying steered pulses to one or more cardiac targets.
Figure 10B:
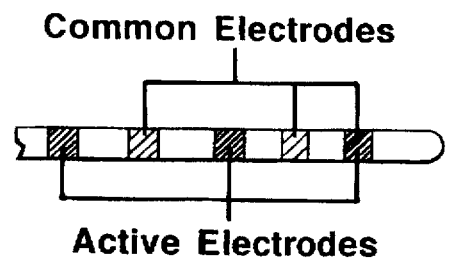
Figure 10C:
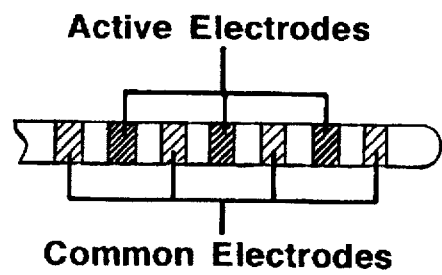
Figure 10D:
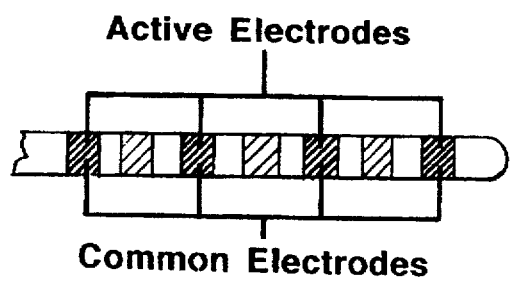
Figure 10E:
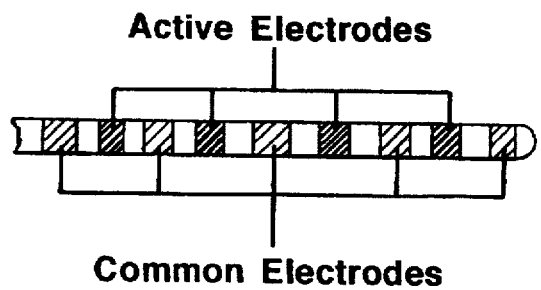
Figure 10F:
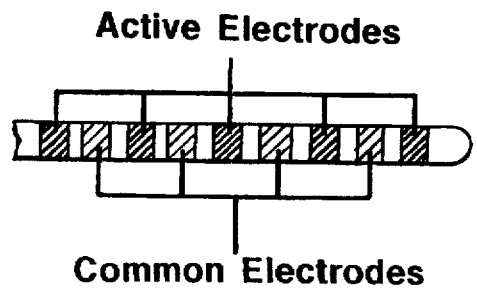

FIGS. 10(a) through 10(f) show some different embodiments of the lead of the present invention. In FIGS. 10(a) through 10(f), active electrodes are shown with solid shading, while common electrodes are shown with hatched shading. FIG. 10(a) shows a lead having two active electrodes and three common electrodes, where both active electrodes are disposed between two outlying common electrodes. FIG. 10(b) shows a lead having three active electrodes separated by two common electrodes. FIG. 10(c) shows a lead having three active electrodes and four common electrodes, where all three active electrodes are disposed between two outlying common electrodes. FIG. 10(d) shows a lead having four active electrodes separated by three common electrodes. FIG. 10(e) shows a lead having four active electrodes and five common electrodes, where all four active electrodes are disposed between two outlying common electrodes. FIG. 10(f) shows a lead having five active electrodes separated by four common electrodes.

It will now become apparent to those skilled in the art that other variations, permutations and combinations of the lead and electrode configurations set forth in FIGS. 1 through 10(f) and described in the specification hereof may be employed in pacing, cardioverting or defibrillating applications, and that such variations, permutations and combinations fall within the scope of the present invention.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

We claim:

1. A pacing system for pacing in at least a patient's left atrium, comprising:

a multiple electrode lead for pacing in the patient's left atrium, said lead having a distal end and at least two anode electrodes and one cathode electrode positioned near said distal end, said electrodes being spaced from each other with a predetermined geometry, said lead having a proximal end for connecting to a pulse generator, and respective conductors connecting the respective electrodes to said proximal end, pulse generator means for generating at least two pulse outputs and delivering a first of said outputs between a first of said anode electrodes and said cathode electrode, and for delivering a second of said outputs between the second of said anode electrodes and said cathode electrode, said pulse outputs having magnitude, polarity and phase parameters, control means for controlling each of said pulse outputs with respect to at least one of said pulse parameters, and steering means for selecting said at least one pulse parameter for each pulse output so as to generate pulses for steering the delivery of composite steering pulses to an effective site when said lead distal end is positioned in the patient's left atrium.

2. The pacing system as described in claim 1, wherein said steering means has means for selecting relative pulse amplitudes for each of the pulse outputs.

3. The pacing system as described in claim 1, wherein said steering means has means for selecting pulse magnitude and pulse polarity for each of said pulse outputs.

4. The pacing system as described in claim 1, further comprising capture detection means for determining when a pair of pulse outputs delivered from said lead electrodes has captured the patient's atrium.

5. The pacing system as described in claim 4, comprising adjusting means for controlling said steering means to adjust said at least one pulse parameter through a predetermined sequence of parameter values, and parameter reset means for resetting said at least one parameter as a function of whether capture is determined for each said parameter value.

6. The pacing system as described in claim 1, wherein said pulse generating means comprises a plurality of pulse generators controllable to generate respective pulse outputs, said lead comprises a plurality of electrodes, and further comprising switching means for switching predetermined ones of said generator outputs to selected ones of said electrodes.

7. The pacing system as described in claim 6, wherein said control means controls said generators to generate a plurality of composite pulses each cardiac cycle, each of said composite pulses being comprised of at least two substantially concurrent pulses controlled with respect to said pulse parameters.

8. The pacing system as described in claim 1, wherein said lead has a first set of electrodes for delivering steering pulses to a patient's atrium and a second set of electrodes for delivering steering pulses to a patient's ventricle.

9. The pacing system as described in claim 1, comprising sensing means for sensing patient natural cardiac signals at selected ones of said electrodes and further comprising sense switching means for switching respective ones of said electrodes to said sense switching means at controlled times.

10. A pacing system for dual chamber pacing of a patient, comprising:

pulse generator means for generating pacing pulses for delivery to the patient's heart, having first pulse means for generating first pacing pulses, said first pulses having controllable respective first magnitude, polarity and phase values, and second pulse means for generating second pacing pulses substantially concurrently with said first pulses, said second pulses having controllable respective second magnitude, polarity and phase values;

a pacing lead connected to said pulse generator means to receive said first and second pulses, said lead having a distal end portion adapted for positioning proximate to or in the patient's heart, said distal end portion having first and second active electrodes and a common electrode, and connecting means for connecting said first pacing pulses between said first electrode and said common electrode and for connecting said second pacing pulses between said second electrode and said common electrode; and control means for controlling said pulse generator means to generate respective steered ventricular and atrial pacing pulses, each of which steered pulses is a combination of a said first and a said second pulse, and steering means for controlling said first and second pulse means so as to select a first set of values of magnitude, polarity and phase for each of said first and second pulses when said pulse generator generates a ventricular pacing pulse, and a second set of values of magnitude, polarity and phase for each of said first and second pulses when said pulse generator generates an atrial pacing pulse.

11. The system as described in claim 10, wherein said control means comprises timing means for controlling the timing of respective generated ventricular and atrial pulses.

12. The system as described in claim 11, comprising sensing means connected to said active electrodes and said common electrode for sensing electrical signals from the patient's heart, and wherein said timing means controls said timing as a function of said sensed electric signals.

13. The system as described in claim 12, comprising additional sensing means located apart from said lead distal end portion for sensing patient cardiac signals, and determining means for determining from said sensed cardiac signals whether they represent atrial or ventricular signals.

14. A pacing system for dual chamber pacing of a patient comprising:
   pulse generator means for generating pacing pulses for delivery to the patient's heart, having first pulse means for generating first pacing pulses, said first pulses having controllable respective first magnitude, polarity and phase values, and second pulse means for generating second pacing pulses substantially concurrently with said first pulses, said second pulses having respective second magnitude, polarity and phase values independently controllable from the first values;
   a single pass pacing lead, said lead having a distal portion for positioning in a patient's right ventricle and an intermediate portion positioned for floating in the patient's right atrium, said intermediate portion having first and second active electrodes and a common electrode, and at least one pacing electrode positioned substantially at the distal portion of said lead, a proximal end for connecting to said pulse generator means, and connecting means for connecting said first pulse signals to said first electrode and said common electrode and said second pulse signals to said second electrode and said common electrode; and
   steering means for controlling said first pulse means with a selected first set of values of magnitude, polarity, and phase and for controlling said second pulse means with a selected second set of values of magnitude, polarity and phase, thereby delivering a steered atrial composite pacing pulse to said patient's right atrium.

15. The system as described in claim 14, further comprising control means for controlling said pulse generator means to generate ventricular pacing pulses, and ventricular connecting means for connecting said generated ventricular pacing pulses to said at least one distal electrode.

16. The system as described in claim 15, wherein said control means comprises timing means for controlling the timing of respective generated ventricular and steered atrial pulses.

17. The system as described in claim 14, further comprising capture detection means for determining when a delivered steered atrial pace pulse achieves atrial capture, and
   threshold detecting means operative together with said capture detection means for determining capture threshold for said steered atrial pulses.

18. The system as described in claim 17, further comprising search means for varying at least one parameters of said first and second pacing pulses of said atrial pulse, and searching for a set of parameter values corresponding to optimum threshold for pacing the patient's atrium.

19. A pacing system for generating and delivering steered composite pace pulses to at least a plurality of sites in a patient's heart, comprising:
   generator means, comprising a plurality of generators for delivering respective stimulus pulse components, each of said generators having outputs controllable with respect to at least the amplitude and polarity of its pulse component;
   electrode means for providing a plurality of electrodes at different respective cardiac positions in the patient's heart, said electrode means providing at least three electrodes constituting two active electrodes and one common electrode at each respective cardiac position;
   a plurality of sense amplifiers for sensing natural heart beat signals from selected ones of said patient positions;
   switch matrix means for connecting selected ones of said generator outputs to respective selected ones of said electrodes, and selected ones of said electrodes to selected ones of said sense amplifiers, said matrix connecting composite stimulus pulses consisting of plural pulse components to selected ones of said positions; and
   pulse parameter and timing control means for controlling the connections made by said switch matrix means, whereby selected cardiac sites receive steered composite stimulus pulses and said composite stimulus pulses are timed as a function of sensed patient natural heartbeat signals.

20. The system as described in claim 19, comprising threshold detection means for detecting when a given one of said composite stimulus pulses results in cardiac capture, and means for controlling said component parameters as a function of said threshold detection.

21. A method of delivering a steered pacing stimulus to at least one site in a patient's heart, comprising:
   storing steering parameter data including at least amplitude and polarity data of at least two pulse components of a steered composite pulse having said at least two components, said at least two components being independently controllable and at least partially overlapping respecting times,
   selecting parameters of said at least two pulse components;
   delivering to said site a composite steered stimulus having said at least two component pulses;
   determining when adjustment of said composite pulse can provide for more effective steering; and
   adjusting said steered composite pulse by changing one or more of said selected pulse component parameters.

22. The method as described in claim 21, comprising initially positioning an array of electrodes within or proximate to the patient's heart, and wherein said delivering step comprises delivering said steered composite pulse across said array of electrodes.

23. The method as described in claim 22, comprising positioning three electrodes within the patient's subclavian vein, wherein said delivering step comprises delivering a two-component pulse, a first of said components being delivered between a first and second of said electrodes, and a second component pulse being delivered between said second and a third of said electrodes.

24. The method as described in claim 23, comprising selecting said pulse component parameters to steer a stimulus pulse to the patent's left atrium.

25. The method as described in claim 22, comprising selecting stimulus parameter data for first and second steered stimulus pulses, and comprising delivering first and second steered stimulus pulses to respective different cardiac targets during a patient cardiac cycle.

26. The method as described in claim 21, comprising selecting said stimulus parameter data for delivering a pacing pulse to a selected one of the patient's heart chambers.

27. The method as described in claim 26, comprising selecting said stimulus parameter data for delivering a defibrillation pulse to the patient's right atrium.

28. The method as described in claim 26, comprising selecting said stimulus parameter data for delivering a defibrillation pulse to the patient's right ventricle.

29. The method as described in claim 21, comprising positioning an array of floating electrodes in the patient's atrium, and wherein said step of delivering a steered stimulus pulse comprises delivering said steered pulse to the patient's atrium by delivering it across said array of floating electrodes.

30. The method as described in claim 21, comprising determining whether a delivered steered atrial stimulus pulse results in atrial capture, and further comprising adjusting said atrial stimulus pulse as a function of whether atrial capture has been sensed.

31. The method as described in claim 21, wherein said step of storing parameter data comprises storing parameter data corresponding to morphology specific therapies, and further comprising the steps of:

detecting a patient arrhythmia;

selecting a therapy as a function of said detected arrhythmia;

retrieving from said stored parameter data parameter data corresponding to the selected therapy; and administering said selected therapy by delivering steered composite pulses having pulse components controlled with said parameter data.

32. An implantable system for delivering pacing stimulus pulses to at least one selected cardiac site in a patient, comprising:

generator means for generating a composite pulse having at least two pulse components;

a lead for delivering said two pulse components to an area in or proximate to the patient's heart, and control means for independently controlling the parameters of each of said pulse components for steering said composite pulse to said selected site, wherein said generator means has means for generating a composite pacing pulse, and said control means comprises parameter adjustment means for adjusting one or more of the amplitude, pulse width and phase of each of said pulse components.

33. The system as described in claim 32, wherein said parameter adjustment means comprises amplitude increment means for incrementing the amplitude of a said pulse component by a predetermined increment.

34. The system as described in claim 33, wherein said parameter adjustment means comprises pulse width means for incrementing the pulse width of a said pulse component by a predetermined increment.

35. The system as described in claim 34, wherein said parameter adjustment means comprises phase means for adjusting the phase of a said pulse component by a predetermined increment.

36. The system as described in claim 32, wherein said lead has at least three electrodes comprising at least two common electrodes and at least one active electrode, and conductor means for delivering a first of said pulse components across a first of said common electrodes and said active electrode and a second of said pulse components across the other of said common electrodes and said active electrode.

37. The system as described in claim 32, wherein said lead has at least three electrodes comprising at least two active electrodes and at least one common electrode, and conductor means for delivering a first of said pulse components across a first of said active electrodes and said common electrode, and a second of said pulse components across the other of said active electrodes and said common electrode.

38. The system as described in claim 37, wherein each of said electrodes is separated by a distance of at least 1 cm.

39. The system as described in claim 37, wherein said two active electrodes are separated by a distance of at least 2 cm.

40. An implantable pacing system, comprising:

a multiple electrode lead for pacing a patient's heart having at least two anode electrodes and at least one cathode electrode positioned thereon, said electrodes being spaced from each other with a predetermined geometry, said lead having a proximal end for connecting to a pulse generator and respective conductors connecting the respective electrodes to said proximal end;

pulse generator means for generating at least two pulse outputs and delivering a first of said outputs between a first of said anode electrodes and said cathode electrode, and for delivering a second of said outputs between a second of said anode electrodes and said cathode electrode, said pulse outputs at least partially overlapping in respect of time and having magnitude, polarity and phase parameters;

control means for independently controlling each of said pulse outputs with respect to at least one of said pulse parameters, and steering means for selecting said at least one pulse parameter for each pulse output so as to generate pulses for steering the delivery of composite steering pulses to an effective site when the electrodes are positioned in the patient's heart.

41. A pacing system, comprising:

a multiple electrode lead for pacing a patient's heart having at least two cathode electrodes and at least one anode electrode positioned thereon, said electrodes being spaced from each other with a predetermined geometry, said lead having a proximal end for connecting to a pulse generator and respective conductors connecting the respective electrodes to said proximal end;

pulse generator means for generating at least two pulse outputs and delivering a first of said outputs between a first of said cathode electrodes and said anode electrode, and for delivering a second of said outputs between a second of said cathode electrodes and said anode electrode, said pulse outputs at least partially overlapping in respect of time and having magnitude, polarity and phase parameters, control means for independently controlling each of said pulse outputs with respect to at least one of said pulse parameters, and steering means for selecting said at least one pulse parameter for each pulse output so as to generate pulses for steering the delivery of composite steering pulses to an effective site when the electrodes are positioned in the patient's heart.

42. A pacing system, comprising:

a multiple electrode lead for pacing in a patient's heart having at least three electrodes of alternating first and second polarities positioned thereon, at least two electrodes having the first polarity, at least one electrode having the second polarity, said electrodes being spaced from each other with a predetermined geometry, said lead having a proximal end for connecting to a pulse generator and respective conductors connecting the respective electrodes to said proximal end;

pulse generator means for generating at least two pulse outputs and delivering a first of said outputs between a first of said at least two first polarity electrodes and said at least one second polarity electrode, and for delivering a second of said outputs between a second of said at least two first polarity electrodes and said at least one second polarity electrode, said pulse outputs having magnitude, polarity and phase parameters;

control means for independently controlling each of said pulse outputs with respect to at least one of said pulse parameters, and steering means for selecting said at least one pulse parameter for each pulse output so as to generate pulses for steering the delivery of composite steering pulses to an effective site when said electrodes are positioned in the patient's heart.

* * * * *